(12) United States Patent
Bolskar et al.

(10) Patent No.: US 7,812,190 B2
(45) Date of Patent: Oct. 12, 2010

(54) DERIVATIZATION AND SOLUBILIZATION OF FULLERENES FOR USE IN THERAPEUTIC AND DIAGNOSTIC APPLICATIONS

(75) Inventors: Robert D. Bolskar, Arvada, CO (US); J. Michael Alford, Lakewood, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 480 days.

(21) Appl. No.: 10/410,809

(22) Filed: Apr. 9, 2003

(65) Prior Publication Data

US 2003/0220518 A1    Nov. 27, 2003

Related U.S. Application Data

(63) Continuation-in-part of application No. 10/263,375, filed on Oct. 1, 2002.

(60) Provisional application No. 60/371,380, filed on Apr. 9, 2002, provisional application No. 60/326,353, filed on Oct. 1, 2001.

(51) Int. Cl.
*C07C 229/00* (2006.01)
*C07C 63/00* (2006.01)
*C07C 51/15* (2006.01)

(52) U.S. Cl. ................ 560/19; 562/405; 562/423; 562/433; 562/445

(58) Field of Classification Search ........ 562/405, 562/433, 423, 445; 560/19; 514/788.1, 789
See application file for complete search history.

(56) References Cited

U.S. PATENT DOCUMENTS

| | | | |
|---|---|---|---|
| 5,475,172 A | 12/1995 | Cahill et al. | 585/27 |
| 5,503,643 A | 4/1996 | Schriver et al. | 44/282 |
| 5,587,476 A | 12/1996 | Kampe et al. | 540/472 |
| 5,648,523 A | 7/1997 | Chiang | 562/100 |

(Continued)

FOREIGN PATENT DOCUMENTS

EP    00695387 A1    2/1996

(Continued)

OTHER PUBLICATIONS

Unknown (1993) "Separating Fullerenes by Electrophoresis," IBM Technical Disclosure Bulletin, vol. 36 No. 06A, Jun. 1993.

(Continued)

*Primary Examiner*—Taylor Victor Oh
(74) *Attorney, Agent, or Firm*—Greenlee, Winner and Sullivan, P.C.

(57) ABSTRACT

The invention provides improved therapeutic and diagnostic fullerenes and endohedral fullerenes. The fullerenes and endohedral fullerenes of the invention are derivatized with at least two charged functional groups (and preferably more than two charged functional groups) to provide for water-solubility and improved in vivo biodistribution. Improved derivatized fullerenes and endohedral fullerenes carry a plurality of functional groups at least two of which are charged. Preferably at least about ⅙ of the possible derivations sites on the fullerene caged carry derivatives and preferably at least about ½ of the functional groups on the fullerene cage are charged groups. The invention also provides water-soluble endohedral metallofullerene with improved biodistribution which are useful as in vivo imaging agents, including MRI contrast agents.

41 Claims, 4 Drawing Sheets

Positive-ion LD-TOF mass spectrum of the "Gd@C$_{60}$ class" of fullerenes; inset is an expansion of the 870 to 900 mass region, showing the isotope patterns for Gd@C$_{60}$ and the empty fullerene, C$_{74}$.

U.S. PATENT DOCUMENTS

| | | | |
|---|---|---|---|
| 5,688,486 A * | 11/1997 | Watson et al. | 424/1.65 |
| 5,717,076 A * | 2/1998 | Yamamoto et al. | 534/558 |
| 5,739,376 A | 4/1998 | Bingel | 560/51 |
| 5,763,719 A | 6/1998 | Gugel et al. | 585/471 |
| 5,811,460 A | 9/1998 | Friedman et al. | 514/563 |
| 5,869,626 A * | 2/1999 | Yamamoto et al. | 534/10 |
| 5,994,410 A | 11/1999 | Chiang et al. | 514/709 |
| 6,020,523 A | 2/2000 | Chiang | 562/493 |
| 6,046,361 A | 4/2000 | Chiang | 564/458 |
| 6,162,926 A * | 12/2000 | Murphy et al. | 548/417 |
| 6,204,391 B1 | 3/2001 | Friedman et al. | 548/338.1 |
| 6,265,443 B1 | 7/2001 | Choi et al. | 514/569 |
| 6,303,016 B1 | 10/2001 | Diener et al. | 205/687 |
| 6,355,225 B1 | 3/2002 | Alford et al. | 424/9.3 |
| 6,399,785 B1 | 6/2002 | Murphy et al. | 548/417 |
| 6,471,942 B1 | 10/2002 | Miller et al. | 424/9.1 |
| 6,517,799 B2 | 2/2003 | Diener et al. | 423/445 |
| 6,613,771 B2 * | 9/2003 | Friedman et al. | 514/256 |
| 2003/0065206 A1 | 4/2003 | Bolskar et al. | 558/87 |

FOREIGN PATENT DOCUMENTS

| | | |
|---|---|---|
| EP | 00782560 A1 | 7/1997 |
| EP | 00695287 B1 | 10/1997 |
| EP | 1071149 A2 | 1/2001 |
| WO | WO 93/15768 | 8/1993 |
| WO | WO94/05671 | 8/1993 |
| WO | WO96/09275 | 9/1994 |
| WO | WO96/26186 | 8/1996 |
| WO | WO96/36631 | 11/1996 |
| WO | WO03/029136 | 4/2003 |

OTHER PUBLICATIONS

Akasaka, T. et al. (1995)(a). "Exohedral Adducts of La@$C_{82}$," *Nature* 374:600-601.

Akasaka, T. et al. (1995)(b). "Synthesis of the First Adducts of the Dimetallofullerenes, La$_2$@$C_{80}$ and Sc$_2$@$C_{84}$ by Addition of a Disilirane," *Angew. Chem. Intl. Ed. Engl.* 34:2139-2141.

Akasaka, T. et al. (1995)(c). "Exohedral Derivatization of an Endohedral Metallofullerene Gd@$C_{82}$," *Chem. Comm.*, pp. 1343-1344.

Balch, A. L.; Olmstead, M. M. (1998). "Reactions of Transition Metal Complexes with Fullerenes ($C_{60}$, $C_{70}$, etc.) and Related Materials" *Chem. Rev.* 98:2123-2166.

Beer, F. et al. (1997). "High-Yield Reactive Extraction of Giant Fullerenes from Soot," *J. Mater. Chem.*, 7:1327-1330.

Bellavia-Lund, C. et al. (1997), "Synthesis of [70] Azafulleroids: Investigations of Azide Addition to $C_{70}$," *J. Am. Chem. Soc.* 119:943-946.

Bethune, D. S. et al. (1993) "Atoms in carbon cages: the structure and properties of endohedral fullerenes," *Nature* 366:123-128.

Beulen, M. W. J. et al. (May 2000). "Adduct Removal from Methanofullerenes via Reductive Electrochemistry," *Chem. Comm.*, pp. 917-918.

Bingel, C. (1993). "Cyclopropanierung von Fullerenen," *Chem. Ber.*, 126:1957-1959.

Bingel, C.; Schiffer, H. (1995). "Biscyclopropanation of $C_{70}$," *Liebigs Ann.*, pp. 1551-1553.

Bolskar, R.D. et al. (Apr. 2003), "First Soluble M@$C_{60}$ Derivatives Provide Enhanced Access to Metallofullerenes and Permit in Vivo Evaluation of Gd@$C_{60}$[C(COOH)$_2$]$_{10}$ as a MRI Contrast Agent," J. Am. Chem. Soc. 125:5471-5478.

Braun, T.; Rausch, H. (1998). "Radioactive endohedral metallofullerenes formed by prompt gamma-generated nuclear recoil implosion," *Chem. Phys. Lett.* 288:179-182.

Brettreich, M.; Hirsch, A. (1998). "A Highly Water-Soluble Dendro[60]fullerene," *Tet. Lett.* 39:2731-2734.

Cagle, W.D. et al. (1996). "Synthesis, Characterization, and Neutron Activation of Holmium Fullerenes," *J. Am. Chem.Soc.* 118:8043-8047.

Cagle, D. W.et al. (1999) "In vivo studies of fullerene-based materials using endohedral metallofullerene radiotracers," *Proc. Natl. Acad. Sci. USA* 96:5182-5187.

Camps, X.; Hirsch, A. (1997). "Efficient Cyclopropanation of $C_{60}$ Starting from Malonates," *J. Chem. Soc. Perkin Trans. 1*, pp. 1595-1596.

Caravan, P. et al. (1999). "Gadolinium(III) Chelates as MRI Contrast Agents: Structure, Dynamics, and Applications," *Chem. Rev.* 99:2293-2352.

Cerar, J. et al. (1998), "Water-Soluble Fullerenes. I. Fullerenehexamalonic Acid $T_h$-$C_{66}$(COOH)$_{12}$, an Intermediate Spherical Electrolyte," *J. Phys. Chem. B* 102(38):7377-7381.

Cheng, F.et al. (May 2000). "Synthesis and Optical Properties of Tetraethyl Methano[60]fullerenediphosphonate," *Tet. Lett.* 41:3947-3950.

Cross, R. J.et al. (1996). "Differentiation of Isomers Resulting from Bisaddition to $C_{60}$ Using $^3$He NMR Spectroscopy," *J. Am. Chem. Soc.* 118:11454-11459.

Diederich, F. et al. (1991) "The Higher Fullerenes: Isolation and Characterization of $C_{76}$, $C_{84}$, $C_{90}$, $C_{94}$, and $C_{70}$O, an Oxide of $D_{5h}$-$C_{70}$," *Science* 252:548-551.

Diederich, F.; Kessinger, R. (1999). "Templated Regioselective and Sterioselective Synthesis in Fullerene Chemistry," *Acc. Chem. Res.* 32:537-545.

Diener, M. D.; Alford, J. M. (1998) "Isolation and Properties of Small-Bandgap Fullerenes," *Nature* 393:668-671.

Dietel, E. et al. (1999). "Atomic Nitrogen Encapsulated in Fullerenes: Effects of Cage Variations," *J. Am. Chem. Soc.* 121:2432-2437.

Dugan, L. L. et al. (Jul. 2000). "Carboxyfullerenes as Neuroprotective Antioxidants," *Fullerenes: Chemistry, Physics, and Technology*, Kadish, K. M. and Ruoff, R. S. eds., John Wiley & Sons, New York, pp. 467-479.

Friedman, S.H. et al. (1993), "Inhibition of the HIV-1 Protease by Fullerene Derivatives: Model Building Studies and Experimental Verification," *J. Am. Chem. Soc.* 115:6506-6509.

Grösser, T. et al. (1995), "Ring Expansion of the Fullerene Core by Highly Regioselective formation of Diazafulleroids," *Angew. Chem. Int. Ed. Engl.* 34(12):1343-1345.

Hawkins, J.M. (1992), "Osmylation of $C_{60}$: Proof and Characterization of the Soccer-Ball Framework," *Acc. Chem. Res.* 25:150-156.

Hinokuma, K.; Ata, M. (Jun. 2001)(a). "Fullerene Proton Conductors," *Chem. Phys. Lett.* 341:442-446.

Hirsch, A. (1999), "Principles of Fullerene Reactivity," in *Topics in Current Chemistry: Fullerenes and Related Structures*, Springer Verlag, Berlin, New York, 199:2-65.

Hirsch, A. et al. (1994), "Regiochemistry of Multiple Additions to the Fullerene Core: Synthesis of a $T_h$-Symmetric Hexakisadduct of $C_{60}$ with Bis(ethoxycarbonyl)methylene," *J. Am. Chem. Soc.* 116:9385-9386.

Hirsch, A. et al. (1992), "Titration of $C_{60}$: A Method for the Synthesis of Organofullerenes," *Angew. Chem. Int. Ed. Engl.* 31(6):766-768.

Hirsch, A. (1994)(a). *The Chemistry of the Fullerenes*, Georg Thieme Verlag Stuttgart, New York.

Hirsch, A.; Lamparth, I.; Karfunkel, H. R. (1994)(b). "Fullerene Chemistry in Three Dimensions: Isolation of Seven Regioisomeric Bisadducts and Chiral Trisadducts of $C_{60}$ Di(ethoxycarbonyl)methylene," Angew. Chem. Int. Ed. 33:437-438.

Illescas, B. et al. (1997), "[60]Fullerene-Based Electron Acceptors with Tetracyano-*p*-quinodimethane (TCNQ) and Dicyano-p-quinonediimine (DCNQI) Derivatives," *Tetrahedron Lett.* 38(11):2015-2018.

Inoue, T. et al. (Jan. 2000). "Electronic Structure of Eu@$C_{60}$ Studied by XANES and UV-VIS Absorption Spectra," *Chem. Phys. Lett.* 316:381-386.

Jung, M. E. (1991). "Stabilized Nucleophiles with Electron Deficient Alkenes and Alkynes," *Comprehensive Organic Synthesis: Selectivity, Strategy, & Efficiency in Modern Organic Chemistry*, Trost, B. M.; Fleming, I. eds., Pergamon Press, Oxford, vol. 4, pp. 1-67.

Kato, T. et al. (1997). "Chemical Reactivities of Endohedral Metallofullerenes," *J. Phys. Chem. Solids* 58:1779-1783.

Kessinger, R. et al. (1998). "Walk On the Sphere: Electrochemically Induced Isomerization of $C_{60}$ Bis-adducts by Migration of Di(alkoxycarbonyl)methano Bridges," *J. Am. Chem. Soc.* 120:8545-8546.

Khong, A. et al. (Apr. 2000). "From $^3He@C_{60}$ to $^3H@C_{60}$: Hot-Atom Incorporation of Tritium in $C_{60}$," *J. Am. Chem. Soc.* 104:3940-3943.

Kitagawa, T. et al. (1999), "Electrophilic Addition of Polychloroalkanes to $C_{60}$: Direct Observation of Alkylfullerenyl Cation Intermediates," J. Am. Chem. Soc. 121:4298-4299.

Klos, H. et al. (1994). "Doping of $C_{60}$ with Tertiary Amines: TDAE, DBU, DBN. A Comparative Study," *Chem. Phys. Lett.* 224:333-337.

Krätschmer, W. et al. (1990) "Solid $C_{60}$: A New Form of Carbon," *Nature* 347:354-358.

Krusic, P.J. et al. (1991), "Radical Reactions of $C_{60}$," *Science* 254:1183-1185.

Kubozono, Y. et al. (1995). "Preparation and Extraction of $Ca@C_{60}$," *Chem. Lett.* pp. 457-458.

Kubozono, Y. et al. (1996)(a). "Extractions of $Ca@C_{60}$ and $Sr@C_{60}$ with Aniline," *Chem. Lett.* pp. 453-454.

Kubozono, Y. et al. (1996)(b). "Extractions of $Y@C_{60}$, $Ba@C_{60}$, $La@C_{60}$, $Ce@C_{60}$, $Nd@C_{60}$, and $Gd@C_{60}$ with Aniline," *J. Am. Chem. Soc.* 118:6998-6999.

Lamparth, I.; Hirsch, A. (1994). "Water-Soluble Malonic Acid Derivatives of $C_{60}$ with a Defined Three-Dimensional Structure," *Chem. Comm.*, pp. 1727-1728.

Lamparth, I. et al. (1997). "Side-Chain Modification of $C_{60}$ via Activation of the Easily Accesible Fulleromalonic Acid $C_{61}(COOH)_2$," Liebigs Ann./Recueil, pp. 253-258.

Liu et al. (1998) "High Efficient Extraction of $M@C_{2n}$ (M=La, Ce) by a High Pressure and High Temperature Method," Tetrahedron 54:11123-11128.

Liu, S.; Sun, S. (Apr. 2000) "Recent progress in the studies of endohedral metallofullerenes," *J. Organomet. Chem.* 599:74-86.

Maggini, M. et al. (1994), "Addition Reactions of $C_{60}$ Leading to Fulleroprolines," *J. Chem. Soc., Chem. Commun*, pp. 305-306.

McHenry, M. E.; Subramoney, S. (Jul. 2000). "Synthesis, Structure, and Properties of Carbon Encapsulated Metal Nanoparticles," in *Fullerenes: Chemistry, Physics, and Technology*, Kadish, K. M. and Ruoff, R. S. eds., John Wiley & Sons, New York, pp. 839-885.

Mikawa, M. et al. (Jun. 2001). "Paramagnetic Water-Soluble Metallofullerenes Having the Highest Relaxivity for MRI Contrast Agents," *Bioconj. Chem.*, 12:510-514.

Moonen, N. N. P. et al. (Mar. 2000). "The Chemical Retro-Bingel Reaction: Selective Removal of Bis(alkoxycarbonyl)methano addends from $C_{60}$ and $C_{70}$ with Amalgamated Magnesium," *Chem. Comm.*, pp. 335-336.

Nagase, S. et al. (1996) "Endohedral Metallofullerenes: New Spherical Cage Molecules with Interesting Properties," *Bull. Chem. Soc. Jpn.* 69:2131-2142.

Nagase, S. et al. (Jul. 2000) "Endohedral Metallofullerenes: Theory, Electrochemistry, and Chemical Reactions," in *Fullerenes: Chemistry, Physics, and Technology*, Kadish, K. M. and Ruoff, R. S. eds., John Wiley & Sons, New York, pp. 395-436.

Nierengarten, J.-F.; Nicoud, J.-F. (1997). "Cyclopropanation of $C_{60}$ with Malonic Acid Mono-Esters," *Tet. Lett.*, 38:7737-7740.

Nierengarten, J.-F. et al. (1997), "Macrocyclization on the Fullerene Core: Direct Regio- and Diastereoselective Multi-Functionalization of [60]Fullerene, and Synthesis of Fullerene-dendrimer Derivatives," *Helv. Chim. Acta.* 80:2238-2276.

Nierengarten, J.F. et al. (1997), "Methanofullerene Molecular Scaffolding: Towards $C_{60}$-$C_{70}$ Hybrid Derivative, and a Novel Macrocyclization Reaction," *Helv. Chim. Acta* 80:293-316.

Nuretdinov, I. A. et al. (Dec. 2000). "Synthesis of Phosphorylated Methanofullerenes," *Russ. Chem. Bull.* 49:2048-2050.

Okada, S.; Saito, S. (Apr. 2000), "Stable Polymers of $C_{74}$ and $C_{78}$ Fullerenes," *Chem. Phys. Lett.* 321:156-162.

Ogawa, T. et al. (Mar. 2000), "Isolation and Characterization of $Er@C_{60}$," *J. Am. Chem. Soc.* 122:3538-3539.

Parker, D. H. et al. (1991). "High-Yield Synthesis, Separation, and Mass-Spectrometric Characterization of Fullerenes $C_{60}$ to C," *J. Am. Chem. Soc.* 113:7499-7503.

Pellicciari, R. et al. (Dec. 2000). "Synthesis of Methano[60]fullerenephosphonic- and Methano[60]fullerenediphosphonic Acids," *Synlett*, pp. 1816-1818.

Prato, M. et al. (1998), "Fulleropyrrollidines: A Family of Full-Fledged Fullerene Derivatives," *Acc. Chem. Res.* 31(9):519-526.

Rapenne, G. et al. (1999). "Regioselective one-step synthesis of trans-3,trans- 3,trans-3 and e,e,e [60]fullerene tris-adducts by $C_3$-symmetrical cyclotriveratrylene tether," *J. Chem. Soc. Chem. Commun.* pp. 1121-1122.

Reed, C. A.; Bolskar, R. D. (Feb. 2000) "Discrete Fulleride Anions and Fullerenium Cations," *Chem. Rev.* 100:1075-1120.

Reuther, U. et al. (May 2002). "A Highly Regioselective Approach to Multiple Adducts of $C_{60}$ Governed by Strain Minimization of Macrocyclic Malonate Addends," *Chem. Eur. J.* 8:2261-2273.

Richardson, C. F. et al. (Mar. 2000). "Synthesis and Characterization of Water-Soluble Amino Fullerene Derivatives," *Org. Lett.* 2:1011-1014.

Ruoff, R. S. et al. (1993) "Solubility of $C_{60}$ in a Variety of Solvents," *J. Phys. Chem.* 97:3379-3383.

Satoh, M. et al. (1997), "Inhibitory Effects of a Fullerene Derivative, Dimalonic Acid C60, on Nitric Oxide-Induced Relaxation of Rabbit Aorta," Eur. J. Pharmacol. 327:175-181.

Schinazi, R.F. et al. (1993), "Synthesis and Virucidal Activity of a Water-Soluble, Configurationally Stable, Derivatized $C_{60}$ Fullerene," *Antimicrob. Agents Chemother.* 37(8):1707-1710.

Shinohara, H. (Jul. 2000). "Endohedral Metallofullerenes: Production, Separation, and Structural Properties," in *Fullerenes: Chemistry, Physics, and Technology*, Kadish, K. M. and Ruoff, R. S. eds., John Wiley & Sons, New York, pp. 357-393.

Shinohara, H. (Jun. 2000). "Endohedral Metallofullerenes," *Rep. Prog. Phys.* 63:843-892.

Skiebe, A. et al. (1994). "[DBU]$C_{60}$. Spin Pairing in a Fullerene Salt," *Chem. Phys. Lett.* 220:138-140.

Stevenson, S. et al. (1999) "Small-bandgap endohedral metallofullerenes in high yield and purity," *Nature* 401:55-57.

Sun, D. et al. (1999) "A Simple Method for the Selective Enrichment of Endohedral Metallofullerenes," *Chem. Mater.* 11:374-377.

Sun, Y.-P. et al. (1997), "Photochemical Preparation of Highly Water-Soluble Pendant (60) Fullerene-Aminopolymers," *Photochem. Photobiol.* 66(3):301-308.

Sun, Y.-P. et al. (1996), "Preparation and Characterization of a Highly Water-Soluble Pendant Fullerene Polymer," *Chem. Commun,.* pp. 2699-2700.

Suzuki, T. et al. (1995). "Chemical Reactivity of a Metallofullerene: EPR Study of Diphenylmethano-La@$C_{82}$ Radicals," *J. Am. Chem. Soc.* 117:9606-9607.

Tagmatarchis, N. et al. (Jul. 2001). "Novel Singlet Oxygen Generators: The Nature and the Number of Trapped Metal Atoms in Endohedral Metallofullerenes M@$C_{82}$ (M=Dy, Gd, La) and $Dy_2@C_{2n}$ (2n=84-94)," *Phys. Chem. Chem. Phys.* 3:3200-3202.

Taylor, R. et al. (1998). "$C_{60}$ Degrades to $C_{120}O$," *Chem. Comm.*, pp. 2497-2498.

Thrash, T.P. et al. (1999). "Toward Fullerene-based Radiopharmaceuticals: High-Yield Neutron Activation of Endohedral $^{165}$Ho Metallofullerenes," *Chem. Phys. Lett.* 308:329-336.

Tokuyama, H. et al. (1993), "Photoinduced Biochemical Activity of Fullerene Carboxylic Acid," *J. Am. Chem. Soc.* 115:7918-7919.

Tomberli, V. et al. (Nov. 2000), "Synthetic Approaches towards the Preparation of Water-Soluble Fulleropyrrolidines," *Carbon* 38:1551-1555.

Tsai, M.-C. (1997), "Polyhydroxylated $C_{60}$, Fullerenol, a Novel Free-radical Trapper, Prevented Hydrogen Peroxide- and Cumene Hydroperoxide-elicited Changes in Rat Hippocampus In-Vitro," *J. Pharm. Pharmacol.* 49:438-445.

Ulmer, L. et al. (1998), "Mono-and Bisfunctionalization of Fullerenes with N-Containing Reactants," *J. Inf. Rec.* 24(3-4):243-247.

Wei, X.-W. et al. (Aug. 2001), "The Remarkable Stable Emerald Green $C_{60}F_{15}[CBr(CO_2Et)_2]_3$: The First [60] Fullerene That Is Also the First [18]Trannulene," *Angew. Chem. Intl. Ed.* 40:2989-2992.

Wharton, T. et al. (Jul. 2001), "New Non-Ionic, Highly Water-Soluble Derivatives of $C_{60}$ Designed for Biological Compatibility," *Tet. Lett.* 42:5159-5162.

Wilson, L. J. (1999). "Medical Applications of Fullerenes and Metallofullerenes," *Electrochemical Society Interface*, Winter Issue, 24-28.

Wilson, S. R. (Jul. 2000)(a). "Biological Aspects of Fullerenes," in *Fullerenes: Chemistry, Physics, and Technology*, Kadish, K. M. and Ruoff, R. S. eds., John Wiley & Sons, New York, 427-465.

Wilson, S. R. et al. (Jul. 2000)(b). "Organic Chemistry of Fullerenes," in *Fullerenes: Chemistry, Physics, and Technology*, Kadish, K. M. and Ruoff, R. S. eds., John Wiley & Sons, New York, 91-176.

Wolff, D.J. et al. (Mar. 2002), "Trisamine $C_{60}$-Fullerene Adducts Inhibit Neuronal Nitric Oxide Synthase by Acting as Highly Potent Calmodulin Antagonists," *Arch. Biochem. Biophys.* 339(2):130-141.

Wolff, D.J. et al. (2001, first published Dec. 2000), "$C_{60}$-Fullerene Monomalonate Adducts Selectively Inactivate Neuronal Nitric Oxide Synthase by Uncoupling the Formation of Reactive Oxygen Intermediates from Nitric Oxide Production," *Biochemistry* 40(1):37-45.

Wolff, D.J. et al. (Jun. 2000), "Inhibition of Nitric Oxide Synthase Isoforms by Tris-Malonyl-$C_{60}$-Fullerene Adducts," *Arch. Biochem. Biophys.* 378(2):216-223.

Wudl, F. (1992), "The Chemical Properties of Buckminsterfullerene ($C_{60}$) and the Birth and Infancy of Fulleroids," *Acc. Chem. Res.* 25(3):157-161.

Yeretzian, C.; Wiley, J. B.; Holczer, K.; Su, T.; Nguyen, S.; Kaner, R. B.; Whetten, R. L. (1993) "Partial Separation of Fullerenes by Gradient Sublimation," *J. Phys. Chem.* 97:10097-10101.

Zhang, S.; Sun, D.; Lix X.; Pei, F.; Liu, S. (1997). "Synthesis and Solvent Enhanced Relaxation Property of Water-Soluble Endohedral Metallofullerenes," *Fullerene Sci. Tech.* 5:1635-1643.

Avent, A. G., et al. (1994), "The structure of $C_{60}Ph_5Cl$ and $C_{60}Ph_5H$ formed via Electrophilic Aromatic Substitution," *J. Chem. Soc., Chem. Comm.*, pp. 1463-1464.

Bensasson, R. V. et al. (Oct. 2001), "Triplet state properties of malonic acid $C_{60}$ derivatives $C_{60}[C(COOR)_2]_n$; R=H, Et; n=1-6," *Phys. Chem. Chem. Phys.* 3:4679-4683.

Bullard-Dillard, R., et al. (1996), "Tissue Sites of Uptake of $^{14}C$-labeled $C_{60}$," Bioorg. Chem. 24:376-385.

Chai, Y. et al. (1991), "Fullerenes with Metals Inside," *J. Phys. Chem.* 95:7564-7568.

Chiang et al. (1992), "Versatile Nitronium Chemistry for $C_{60}$ Fullerene Functionalization," *J. Amer. Chem. Soc.* 114:10154-10157.

Diener, M. D. et al. (1997), "Anaerobic Preparation and Solvent-Free Separation of Uranium Endohedral Metallofullerenes," *Chem. Mater.* 9:1773-1777.

Dugan, L. L. et al. (1997), "Carboxyfullerenes as Neuroprotective Agents," *Proc. Natl. Acad. Sci. USA* 94:9434-9439.

Edelson, E. (1991), "Buckyball the Magic Molecule," *Popular Sci.*, pp. 52-57, 87.

Fatin-Rouge, N. et al. (Oct. 2000), "Lanthanide Podates with Programmed Intermolecular Interactions: Liminescence Enhancement through Association with Cyclodextrins and Unusually Large Relaxivity of th Gadolinium Self-Aggregates," *J. Am. Chem. Soc.* 122:10810-10820.

Feng, L. et al. (Oct. 2002), "Chemical Modification of $Tb@C_{82}$ by Copper (I)-Catalyzed Cycloadditions," *Chem. Mater.* 14:4021-4022.

Grösser, T. et al. (1995), "Ring Expansion of the Fullerene Core by Highly Regioselective Formation of Diazafulleroids," *Angew. Chem. Int. Ed. Engl.* 34(12):1343-1345.

Guldi, D. M. et al. (1995), "Unusual Redox Behavior of a Water Soluble Malonic Acid Derivative of $C_{60}$: Evidence for Possible Cluster Formation," *J. Phys. Chem.* 99:13487-13493.

Guldi, D. M. et al. (1997), "Radiolytic Reduction of a Water-Soluble Fullerene Cluster," *J. Phys. Chem. A* 101:1783-1786.

Guldi, D. M. (1997), "Capped Fullerenes: Stabilization of Water-Soluble Fullerene Monomers As Studied by Flash Photolysis and Pulse Raiolysis," *J. Phys. Chem. A* 101:3895-3900.

Hettich, R. et al. (1999), "Investigation of the fragmentation and oxygen reactivity of endohedral metallofullerenes $M@C_{60}$," *Int. J. Mass. Spec.* 182/183:335-348.

Hoke, S.H. et al. (1994), "Pyrolytic Synthese of a $C_{60}$ Derivative of Naphthalene and Some Congeners" *J. Org. Chem.* 59:3230-3231.

Illescas, B. et al. (1997), "Fullerene-Based Electron Acceptors with Tetracyano-p-quinodimethane (TCNQ) and dicyano-p-quinonediimine (DCNQI) Derivatives," *Tetrahedron Lett.* 38:2015-2018.

Jeng, U.-S.; et al. (Nov. 2001), "Comparison of the aggregation behavior of water-woluble hexa(sulfobutyl) fullerenes and polyhydroxylated fullerenes for their free-radical scavenging activity," *Progr. Colloid Polym. Sci.* 118:232-237.

Jeng, U.-S. et al. (1999), "Study of Aggregates of Fullerene-Based Ionomers in Aqueous Solutions Using Small Angle Neutron and X-ray Scattering," *J. Phys. Chem. B* 103:1059-1063.

Kanbara, T. et al. (Aug. 2001), "$Dy@C_{60}$: Evidence for endohedral structure and electron transfer," *Phys. Rev. B* 64:113403-1-113403-3.

Kato, H. et al. (Nov. 2001), "Syntheses and Biological Evaluations of α-D-Mannosyl [60]Fullerenols," Bioorg. Med. Chem. Lett. 11:2935-2939.

Kessler, B. et al. (1997), "Evidence for Incomplete Charge Transfer and La-Derived States in the Valence Bands of Endohedrally Doped $La@C_{82}$," *Phys. Rev. Lett.* 79:2289-2292.

Lauffer, R.B. (1987), "Paramagnetic Metal Complexes as Water Proton Relaxation Agents for NMR Imaging: Theory and Design," *Chem. Rev.* 87:901-927.

Lin, A.M.Y. et al. (1999), "Carboxyfullerene Prevents Iron-Induced Oxidative Stress in Rat Brain," *J. Neurochem.* 72(4):1634-1640.

Mohan, H. et al. (1998), "Excited states and electron transfer reactions of $C_{60}(OH)_{18}$ in aqueous solution," *J. Chem. Soc., Faraday Trans.* 94(3):359-363.

Qingnuan, L. et al. (Aug. 2002), "Preparation of $^{99m}Tc$-$C_{60}(H)_x$ and its biodistribution studies," *Nucl. Med. Biol.* 29:707-710.

Sawamura, M., H. Iikura, E. Nakamura (1996) The First Pentahaptofullerene Metal Complexes, J. Am. Chem. Soc. 118:12850-12851.

Sawamura, M. et al. (Apr. 2000) Single-step synthesis of pentaaryl-monohydro[60]fullerenes through fivefold addition of organocopper reagent to C60, J. Orgmetallic Chem. 599 32-36.

Shinohara, H. et al. (1993), "Isolation and Spectroscopic Properties of $Sc_2@C_{74}$, $Sc_2@C_{82}$, and $Sc_2@C_{84}$," *J. Phys. Chem.* 97:4259-4261.

Solodovnikov, S. P. et al. (Nov. 2001), "Spectral study of reactions of $La@C_{82}$ and $Y@C_{82}$ with amino-containing solvents,"*Russ. Chem. Bull.* 50:2242-2244.

Tóth, E.; Helm, L., Merbach, A. (Jun. 2001), "Relaxivity of Gadolinium (III) Complexes: Theory and Mechanism," in *The Chemistry of Contrast Agents in Medical Magnetic Resonance Imaging*; Merbach, A.; Tóth, E., Eds.; John Wiley & Sons: Chichester, pp. 45-120.

Wedeking, P. et al. (1990), "Pharmacokinetic Analysis of Blood Distribution of Intravenously Adminstered $^{153}Gd$-Labeled $Gd(DTPA)^{2-}$ and $^{99m}Tc(DTPA)$ in Rats," *Magn. Res. Imag.* 8:567-575.

Wilson, L. J. et al. (1999), "Metallofullerene drug design," *Chem. Rev.* 190-192:199-207.

Yamago, S, H. et al. (1995) "In vivo biological behavior of a water-miscible fullerne: $^{14}C$ labeling, absorption, distribution, excretion and acute toxicity," Chemistry & Biology 2(6)385-389.

Zhou, S. et al. (Mar. 2001), "Spherical Bilayer Vesicles of Fullerene-Based Surfactants in Water: A Laser Light, Scattering Study," *Science* 291:1944-1947.

\* cited by examiner

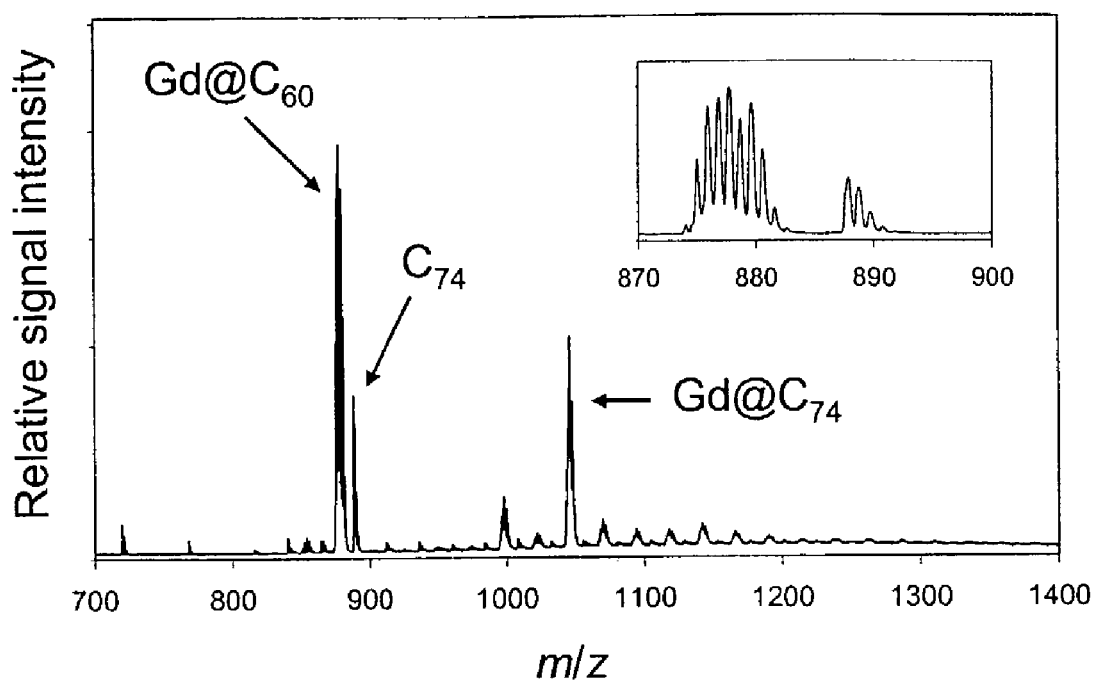
Figure 1. Positive-ion LD-TOF mass spectrum of the "Gd@$C_{60}$ class" of fullerenes; inset is an expansion of the 870 to 900 mass region, showing the isotope patterns for Gd@$C_{60}$ and the empty fullerene, $C_{74}$.

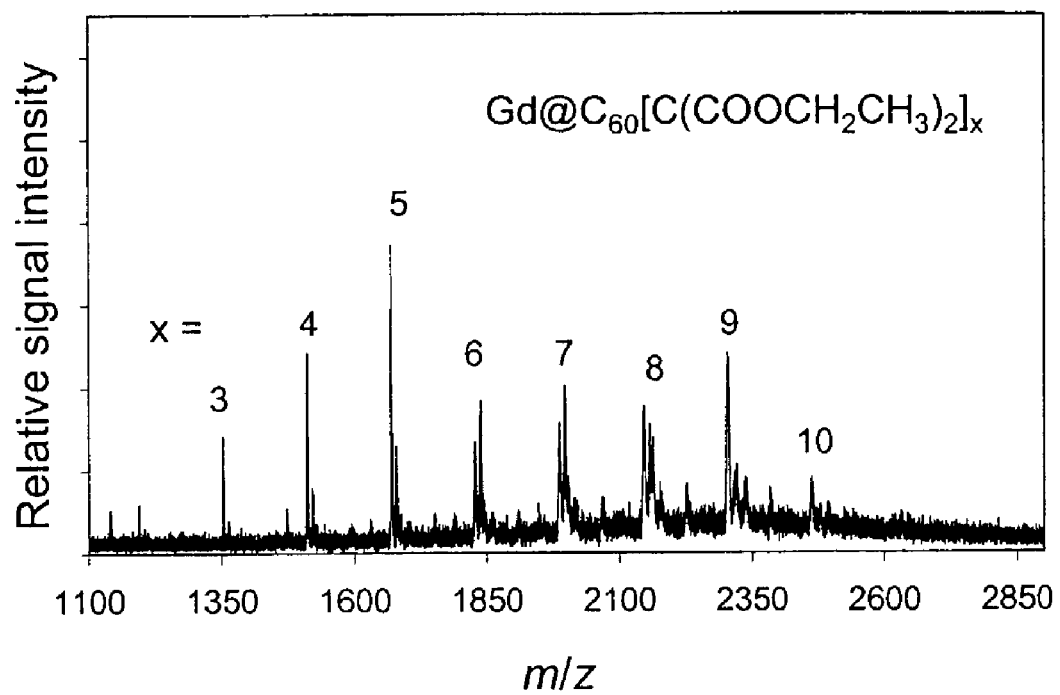
Figure 2. Positive-ion MALDI-TOF mass spectrum of the $Gd@C_{60}[C(COOCH_2CH_3)_2]_{10}$ derivative product ($S_8$ matrix); x = 10 derivative groups corresponds to the parent peak, with the lesser x peaks due to molecular fragments formed by the laser desorption process.

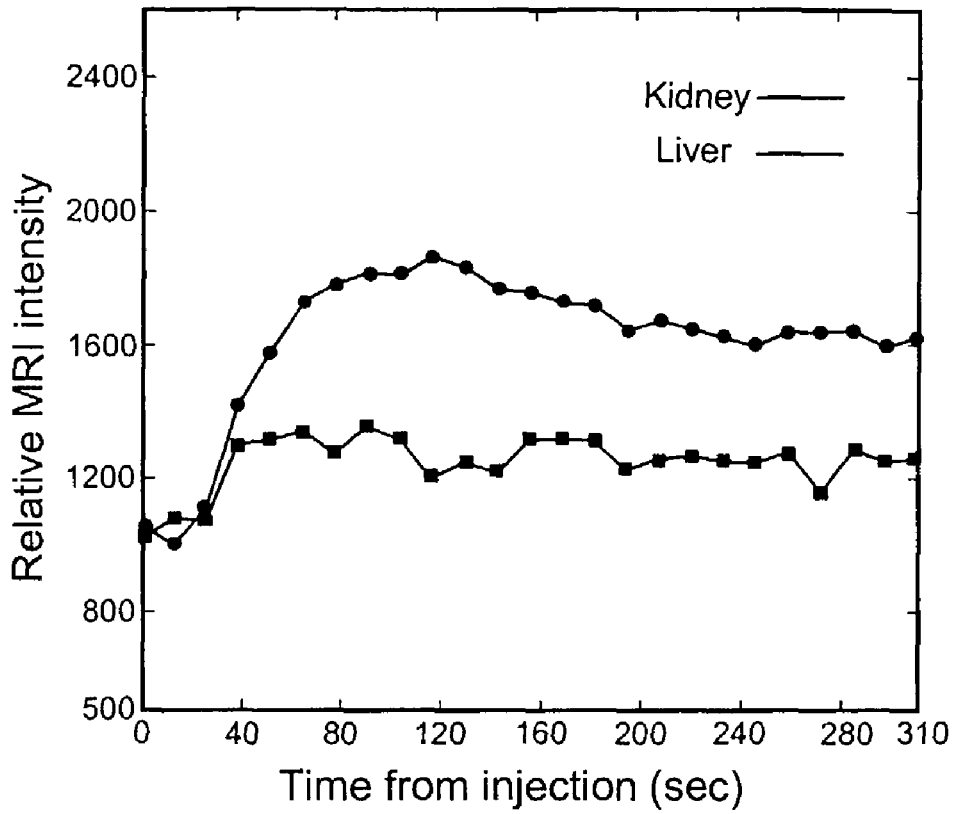
Figure 3. Representative in vivo MRI intensity-derived biodistribution data showing the $Gd@C_{60}[C(COOH)_2]_{10}$ signal enhancement within the first five minutes of administration, revealing rapid renal uptake with a minimum of liver uptake (red filled circles, kidney; blue filled squares, liver).

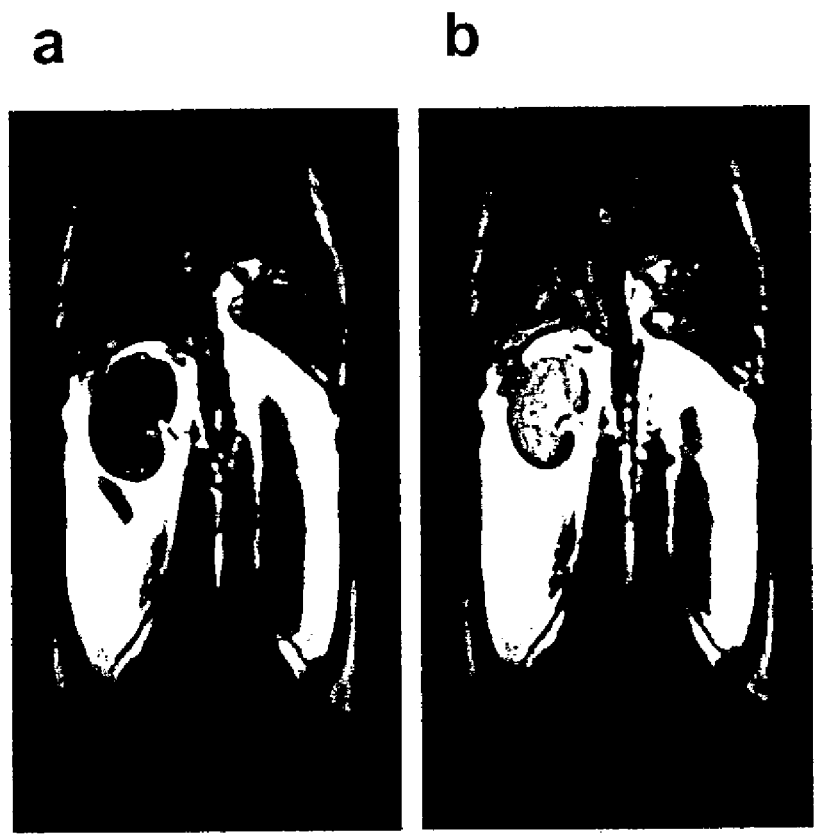
Figure 4. Representative in vivo rodent MR images focusing on a cross section containing a portion of one kidney. a, baseline image without contrast agent; b, image of the same cross section 16 min after administration of $Gd@C_{60}[C(COOH)_2]_{10}$ with increased signal intensity in the kidney.

DERIVATIZATION AND SOLUBILIZATION OF FULLERENES FOR USE IN THERAPEUTIC AND DIAGNOSTIC APPLICATIONS

CROSS-REFERENCE TO RELATED APPLICATIONS

This application takes priority under 35 U.S.C. §119(e) from U.S. provisional application 60/371,380, filed Apr. 9, 2002, which is incorporated by reference in its entirety herein. This application is further a continuation-in-part of U.S. patent application Ser. No. 10/263,375, filed Oct. 1, 2002 which in turn claims priority under 35 U.S.C. §119(e) from U.S. provisional application 60/326,353, filed Oct. 1, 2001. Both of these applications are incorporated by reference in their entirety herein.

STATEMENT REGARDING GOVERNMENT SUPPORT

This invention was made under a grant from the United States government through the National Institutes of Health Grant No. 5R44CA066363-03. The United States government has certain rights in this invention.

BACKGROUND OF THE INVENTION

This invention relates generally to derivatized fullerenes useful for therapeutic and in vivo diagnostic applications which exhibit improved biodistribution. In particular, the invention relates to methods of making and using such derivatives and more particularly to the use of such derivatives for improved magnetic resonance imaging (MRI).

The use of fullerenes as diagnostic and therapeutic compounds has been discussed in the open literature since at least 1991. A suggestion for the use of $C_{60}$ in cancer diagnosis and therapy even appeared in *Popular Science Magazine* (Edelson 1991). U.S. Pat. No. 5,994,410 (Long et al.) relates to therapeutic use of certain water-soluble fullerene derivatives F—(X)m where F is the fullerene core, m is 2-40, X is OH, $(CH_2)$n-$SO_3H$, or a metal salt of $(CH_2)$n-$SO_3^-$ and n is 2-50 for treating a free radical-related medical condition.

U.S. Pat. No. 5,688,486 issued Nov. 18, 1997 by Watson et al. based upon a PCT WO/93/15768, published Aug. 19, 1993 relates to the use of fullerenes and metallofullerenes for diagnostic and therapeutic applications. The patent provides a number of examples of fullerenes that are purported to be useful as carriers for diagnostic or therapeutic agents. Examples include $C_{60}F_{n'}$ where n' is 30 to 60 for use as a PET contrast agent; $Mt_n@C_m$ (Mt=lanthanide, transition or rare earth metal, m=60, 80, 82, 84, 92, 106 etc., and n=1, 2, etc.) with paramagnetic cage complexes useful as MRI contrast agents and certain other metal cage complexes (lanthanum, iridium and lutetium) useful in photodynamic therapy; polyiodinated $C_{60}$ useful as an X-ray contrast agent; $C_{60}(CH_2C_6H_5)_{n'}$ n'=3,5 radical useful as MRI contrast agents; polyhydroxylated Gd@$C_{60}$ prepared by the method of Chiang et al., 1992; Gd@$C_{82}$ reported to be derivatizable by the method of Chiang et al., 1992; Gd@$C_{60}$ imbedded in cyclodextrin for use in MR imaging (also M@$C_{60}$ where M is Dy, Ho, La, Lu, and other rare earth metals); osmylated fullerene for tissue staining; $\{[(C_2H_5)_3P]_2Pt\}_6C_{60}$ for use as an X-ray contrast medium; sugar-labeled fullerenes for enzyme assays; (eta-5-$C_9H_7$)Ir(CO)($C_{60}$) for photodynamic therapy for cancer; isotopically-labeled fullerenes (carbon-14 enriched $C_{60}$) as a source of countable radiation in a diagnostic test; fluorinated fullerenes for use in NMR imaging; $C_{60}$ species labeled with carborane units for use in anticancer therapy using neutron irradiation; and $^{111}$In@$C_{80}$ useful as a radiation source for SPECT imaging; $C_{60}Br_{24}$ for use in CT scanning. The patent notes the use of fullerene materials as contrast-enhancing agents in MRI, ultrasound, PET, Overhauser MRI, scintigraphy, X-ray, CT, SPECT, magnetometric tomography, EIT, visible and it imaging and as carriers for signal reporters, such as chromophores, fluorophores or radiolabels as well as in in vitro assays and for tissue staining. The patent further notes therapeutic applications of fullerene materials to carry and release therapeutically active molecules or atoms or in photodynamic therapy or radiotherapy or as therapeutically active bioconjugates.

U.S. Pat. No. 6,265,443 reports a method for treatment of neurotoxic injury resulting form the release of oxygen-derived free radicals using carboxylated derivatives of $C_{60}$(C(COOH)$_2$)$_n$, where n is 1-4.

U.S. Pat. Nos. 5,811,460 and 6,204,391 report water soluble derivatives of $C_{60}$ for inactivation of HIV. The derivatives a re generally described as symmetrically substituted with organic moieties comprising from 1 to about 20 carbon atoms each and optionally comprising polar heteroatoms, such as oxygen and nitrogen. The patents illustrate the structures of a number exemplary derivatized $C_{60}$ molecules with substituent groups added at one or two of the double bonds of the fullerene. An exemplary derivatized $C_{60}$ is designated 4,4'-bis(HOC(O)(CH$_2$)$_2$C(O)NH(CH$_2$)$_2$-)diphenyl-$C_{61}$.

U.S. Pat. Nos. 6,162,926 and 6,399,785 relate to multiply-substituted fullerene derivatives and to methods of producing a large number of multiply-substituted fullerene derivatives to generate combinatorial libraries wherein some of the compounds of the library are purported to possess pharmaceutical, materials science, or other utilities. The patent provides methods and lists references providing methods for derivatization of fullerenes, for example, via various cycloaddition reactions (1,3-dipolar additions, Diels-Alder reactions, etc.), cyclopropanation by addition/elimination and by addition of carbanions, alkyl lithium reagents or Grignard reagents. These patents are incorporated by reference herein specifically for the derivatization methods described and referenced therein and for structures of derivatized fullerenes that are illustrated therein.

U.S. Pat. No. 6,355,225 relates to the use of water-soluble, air-stable paramagnetic fullerenes having an unpaired electron useful as contrast agents for MRI imaging and spectroscopy. The fullerenes of the invention are exemplified by fullerols and particularly by radicals of $C_{60}$(OH)$_x$ (where x is 12 or 32). The patent reports a relaxivity ($r_1$) measurement of 0.5 mM$^{-1}$ sec$^{-1}$ for the –1 or –2 anion of $C_{60}$(OH)$_{32}$.

Several different groups have identified water-solubilized polyhydroxyl Gd metallofullerene compounds as potential MRI contrast agents Zhang et al. 1997; Wilson et al., 1999; Mikawa, et al., 2001.)

U.S. Pat. No. 6,471,942 relates to the use of trimetallic nitride endohedral metallofullerenes having at least one diagnostic atom and at least one treatment atom encapsulated within a fullerene cage for imaging and treating an area of the body. The patent indicates generally that the fullerene of the patent may be "modified to enhance absorption" in the body and in target tissues by attaching at least one functional group to the fullerene cage. Functional groups selected from "an aminosubstituted group, a carboxyl group, a hydroxyl group, a polyethylene glycol complex, carbohydrates, amino acids, proteins, nucleic acids, markers and antibodies."

While the general idea for the use of fullerene and metallofullerene compounds having utility in medicine and diagnostics has been discussed in the prior art, with emphasis on MRI applications, few of the compounds synthesized and indicated to be useful for such applications to date have significant utility in general for such applications because they are not sufficiently water-soluble.

In addition to being extremely hydrophobic, metallofullerene molecules have a strong propensity to polymerize and/or to aggregate when in water. The hydroxyl groups suggested in the prior art for water solubilization do not prevent aggregation, as a result the polyhydroxylated metallofullerenes are nano-aggregates that range in size from 10-100 nm or larger. When introduced in-vivo, the body's reticuloendothelial system recognizes that these compounds are actually small particles, not individually solvated molecules. They are subsequently encapsulated by phagocytosis and carried to the RES tissues (liver, spleen, bone marrow and lymph nodes). This pharmacokinetic (PK) behavior is unsuitable for broad use in medical imaging. This PK behavior is also not desirable for general MRI contrast agents, although it may be acceptable for RES contrast agents.

Biodistribution studies of the polyhydroxylated metallofullerenes have recently revealed high uptake levels of these compounds by the reticuloendothelial system (RES). A radiotracer study conducted by Cagle et al., 1999 with $^{166}Ho_n@C_{82}(OH)_x$ (n=1, 2; x~16) showed significant RES uptake in mice, including concentration of the polyol in liver and bone. An MR imaging and biodistribution study by Mikawa et al., 2001 with $Gd@C_{82}(OH)_x$ (x~40) reported similar results. A radiotracer study with the (reportedly non-endohedral) polyhydroxyl $C_{60}$ derivative $^{99m}Tc-C_{60}(OH)_x$ in mice and rabbits also showed significant uptake of the polyhydroxyl fullerene by the kidneys, bone, spleen and liver (Qingnuan et al, 2002.) In spite of the reported high $r_1$ values for the polyhdroxylated metallofullerenes, these biodistribution studies indicate that these fullerenes (e.g., $Gd@C_{82}(OH)_x$, and $Ho@C_{82}(OH)$), will only have limited use as MRI contrast agents, i.e. for imaging the reticuloendothelial system (liver, spleen, bone marrow)

Two reports on in vivo absorption, distribution and excretion of fullerenes are consistent with the recent biodistribution results reported for polyhydroxylated metallofullerenes. Yamago et al., 1995 relates to studies using two water-soluble mono-derivatized $C_{60}$ compounds 1 and 2:

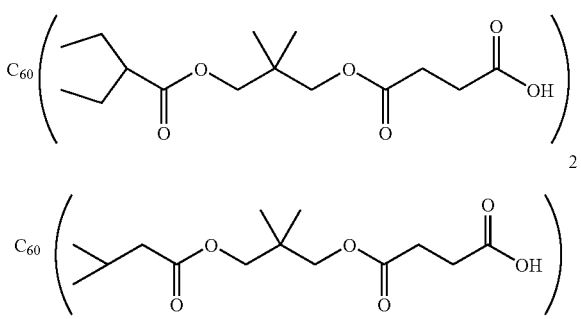

Compound 1 (radioactively labeled with $^{14}C$) was reported to not be effectively absorbed when administered orally, but the small amount absorbed moved quickly to the liver and to other tissues and thereafter excretion was slow with over 90% of what was absorbed retained in the body after one week. When delivered intravenously, 73% of radioactively labeled compound 1 was found in the liver after 1 h and 80% of the radioactivity was retained in the liver after 30 h. From 30-160 h the radioactivity in the various organs decreased but was distributed in skeletal muscle and hair, without excretion from the body. Compound 2 was found to exhibit no acute toxicity. Although fullerene 2 did not exhibit acute toxicity, the authors state that the administered fullerene was retained in the body for long periods which "raise new concerns about chronic toxicity."

Bullard-Dillard et al., 1996 reported that $C_{60}$ intravenously injected into rats as a fine suspension in water and a more water soluble quaternary ammonium salt derivatized $C_{60}$ injected as an ethanol-containing solution both predominantly accumulated (90-95% and 52%, respectively) in the liver. Further $C_{60}$ was reported not to be eliminated from the liver over the 120-h period of the study. The authors state, based on their results, that while $C_{60}$ is not acutely toxic its use in vivo would likely lead to long-term accumulation in the liver.

To realize the full potential of the fullerene and metallofullerene compounds in medicine and diagnostics, other derivatives that are eliminated through the kidneys in a shorter time frame and which do not accumulate in the RES tissues are needed.

SUMMARY OF THE INVENTION

This invention provides water-soluble fullerenes and endohedral fullerenes, including metalloendohedral fullerenes exhibiting improved biodistributions which are useful in therapeutic and diagnostic (particularly in vivo diagnostic) applications. The invention provides derivatization methods which result in the production of fullerenes and endohedral fullerenes, including endohedral metallofullerenes, which exhibit biodistribution in which RES uptake is minimized. The derivatization methods herein are particularly useful for derivatizing those fullerenes that are normally insoluble and which are specifically applicable to endohedral fullerenes (including endohedral metallofullerenes and particularly to the endohedral metallo-$C_{60}$) and to very high molecular weight fullerenic materials generated in fullerenic soot, including metal-carbon nanoencapsulates.

Derivatives formed by the methods herein exhibit decreased aggregation or polymerization in solution resulting in improved biodistribution and decreased uptake in vivo by the RES. Derivatives herein may also exhibit increased water-solubility. Fullerenes derivatized by the processes herein exhibit improved biodistribution as a result of increased solubility and/or the reduced tendency to aggregate or polymerize in aqueous solutions. The methods of this invention can also be generally applied to the further derivatization of water-soluble metallofullerenes to decrease aggregation, to improve their biodistribution or to increase their water-solubility. The methods herein are further specifically applicable to derivatization of empty small band gap fullerenes, particularly $C_{74}$; $C_{72}$, $C_{80}$; and generally $C_{2n}$ with 2n from 74 to 100, and giant small-bandgap fullerenes with $C_{2n}$ (2n greater than 100).

The derivatization methods herein can more specifically be applied to form water-soluble derivatives of endohedral metallofullerene which exhibit improved biodistribution as a result of increased solubility and/or the reduced tendency to aggregate or polymerize in aqueous solutions. In specific embodiments, the metallofullerene derivatives are those having a $C_{60}$, $C_{70}$, $C_{74}$, $C_{82}$ or $C_{84}$ fullerene cage.

In specific embodiments, the methods herein provide endohedral fullerene derivatives for use in therapeutic applications, medical imaging techniques, and particularly in non-RES MRI imaging, and for targeting of metals and other atoms or molecules within the fullerene cage selectively to types of cells or types of tissues, which exhibit improved biodistribution, particularly derivatives of normally insoluble fullerenes, and particularly derivatives of endohedral fullerenes with one or more (typically two) metal elements. Metal elements can be lanthanide metals (Ce, Pr, Nd, Sm, Eu, Gd, Th, Dy, Ho, Er, Tm, Tm, Yb, Lu, La, Sc and Y), actinide metals (Ac, Th, Pa, U, Np, Pu, Am, etc.), transition metal (Cu, Sc, Y, Zr, Hf, etc.); alkali metals (Li, Na, K, Rb, Cs) or alkaline earth metals (Be, Mg, Ca, Sr, Ba, Ra) and also including radioactive, magnetic or paramagnetic metals. Other atoms can be within the endohedral fullerene for example Sb, I, Bi, At, the noble gas elements (He, Ne, Ar, Kr, Xe, and Rn) or NMR active atoms (e.g., $^{3}$He, $^{31}$P, $^{13}$C, $^{15}$N, $^{11}$B, $^{19}$F.) Endohedral fullerenes of this invention include radionuclear endohedral fullerenes, including among others, endohedral fullerenes containing $^{61}$Cu, $^{64}$Cu, $^{67}$Cu, $^{177}$Lu, $^{133}$Xe, $^{141}$Ce, $^{147}$Nd, $^{160}$Tb, $^{161}$Tb, $^{166}$Ho, $^{169}$Er, $^{170}$Tm, $^{175}$Yb, $^{223}$Ra, $^{225}$Ra, $^{225}$Ac, $^{227}$Th, $^{233}$Pa, $^{212}$Bi, $^{213}$Bi, $^{212}$Pb, $^{211}$At, or $^{222}$Rn. Radionuclear endohedral fullerenes derivatives of this invention are useful in both therapeutic and diagnostic applications.

The invention also provides methods of using the water-soluble derivatized fullerenic species of the invention which exhibit minimal aggregation and/or improved biodistribution for therapeutic and/or diagnostic applications. Endohedral metallofullerenes with functional groups that provide improved solubility, reduced tendency to aggregate or improved biodistribution are particularly useful as paramagnetic contrast enhancing agents for magnetic resonance imaging (MRI), or for use in radiotracer studies or in other imaging techniques. Derivatives made by the methods of this invention can, for example, be particularly useful as blood pool contrast agents. Containment of the paramagnetic or other metal (such as a lanthanide metal ion, e.g., $Gd^{3+}$) useful for therapy or diagnostics within the fullerene under physiological conditions prevents dissociation of the metal ion into the patient, providing reduced toxicity when compared to conventional metal coordination complexes and chelates.

In preferred embodiments the methods herein are used to generate water-soluble fullerenes derivatized with a plurality (two or more) functional groups (which are alternatively designated substituents) wherein at least two of the plurality of functional groups are charged groups. The charged functional groups on the fullerene may be of like charge (either all anionic or all cationic) or the fullerene maybe substituted with a mixture of cationic functional groups and anionic functional groups. A fullerene or metallofullerene that is substituted with charged groups may be a charged, neutral or zwitterionic species. Charged functional groups are those that are charged under the conditions in which the fullerenes will be employed, e.g., at physiologic pH. Also in preferred embodiments the number of functional groups and the number of those functional groups that are charged on the fullerene increases with increasing size of the fullerene cage.

For example, generally for a fullerene or endohedral fullerene with fullerene cage of formula $C_{2n}$ (where n is an integer equal to or greater than 25 or more preferably 30) there are n double bonds on the fullerene surface that can be derivatized. Each double bond can be derivatized with up to two non-hydrogen groups. The maximum number of non-hydrogen groups that can be added to the fullerene surface is thus 2n. In preferred fullerenes and endohedral fullerenes of this invention at least about ⅙ of the double bonds on the fullerene cage carry at least one non-hydrogen functional group and at least about ⅓ of the functional groups on the double bonds are charged groups. (When ⅙ of the double bonds or ⅓ of the functional groups calculated for a given fullerene material is not an integer, the calculated number is rounded up to the next highest integer.) For example, for a $C_{60}$ fullerene or endohedral metallofullerene, preferably at least 5 double bonds of the fullerene carry at least one non-hydrogen functional group and at least ⅓ of the 5 functional groups (1.8) rounded up to 2 of the functional groups are preferably charged functional groups.

In more preferred embodiments, at least about ⅓ of the double bonds on the fullerene cage carry at least one non-hydrogen functional group. In other more preferred embodiments, at least about ½ of the non-hydrogen functional groups on the fullerene are charged groups. In specific embodiments, all of the functional groups on the fullerene are charged groups, which may have like charges (all cationic or all anionic) or different charges (some cationic and some anionic). Charged groups are those that are charged under conditions in which the fullerene will be employed and in particular are those which are charged at physiologic pH. Non-charged functional groups on the fullerene or endohedral fullerene may be selected to be non-polar or polar and/or hydrophilic to enhance solubility of the fullerene or endohedral fullerene in water.

Functional groups that can be introduced onto the fullerene surface include among others those containing one or more highly polar or ionized groups such as carboxylic acid groups (—COOH), carboxylates (—COO$^{-}$), alkyl or aryl groups substituted with one or more carboxylic acid groups or carboxylates (e.g., carboxy-substituted phenyl groups), ether or ether groups substituted with carboxylic acid groups or carboxylate groups (e.g., functional groups of compounds 1 and 2), amino groups (—N(R)$_{2}$) or quaternary ammonium cations (—N(R)$_{3}^{+}$), or alkyl or aryl groups substituted with one or more carboxylic acid groups or carboxylates (e.g., carboxy-substituted phenyl groups) where R independent of other R is hydrogen, alkyl, aryl or alkenyl groups. R groups of the quaternary ammonium cations may themselves be substituted with polar groups, including CO, OCO, N(R)$_{2}$, halogen (F, Cl, Br, I) or OH groups. Preferred substituents are selected to increase solubility and minimize aggregation and are compatible with other substituents and the intended use of the fullerene.

In specific embodiments herein, the charged functional groups attached to the fullerene or endohedral fullerene can be alkyl or aryl groups substituted with one or more carboxylic acid groups or carboxylate groups. Of particular interest are charged functional groups that are carboxy-substituted aryl and carboxy-substituted phenyl groups. Aryl groups, in general, and phenyl groups and substituted phenyl and aryl groups, more specifically can be covalently attached to the fullerene cage of empty or endohedral fullerenes employing methods as illustrated in Avent et al., 1994; Sawamura et al., 1996 or Sawamura et al., 2000, or by other means known in the art. More than 2 carboxy-substituted phenyl or aryl groups can be bonded to fullerenes. Preferably 5 or 10 carboxy-substituted phenyl or aryl groups can be bonded to fullerenes. Structures of phenyl-substituted fullerenes are illustrated in Avent et al., 1994; Sawamura et al., 1996 or Sawamura et al., 2000.

Preferred derivatized fullerenes carry two or more charged (or ionized) groups. Charged groups include carboxylate groups can be in the form of carboxylate salts-COO$^{-}$A$^{+}$, or dicarboxylate salts, >C(COO$^{-}$)$_{2}$B$^{2+}$, where A$^{+}$ and B$^{2+}$ are appropriate mono- and dications, such as an alkali metal cations (Li$^{+}$, Na$^{+}$, K$^{+}$, Rb$^{+}$, and Cs$^{+}$), alkaline earth metal dications (e.g., Mg$^{2+}$); or organic-based mono and dications such as quaternary ammonium cations and other substituted ammonium species, including cationic amino acid residues. Quaternary ammonium cations can be in the form of salts —$N(R)_3^+D^-$ or where $D^-$ is an appropriate anion (which can be a mono charged anion or a multiply charged anion), such as halides (e.g., $Cl^-$), sulfates, bisulfates, phosphates, anions of organic mono and diacids, acetate, maleate, fumarate, oxalate, lactate, tartrate, citrate, gluconate, methane-sulfonate, 4-toluene-sulfonate. Anions and cations employed in salts for medical imaging, therapeutic or diagnostic assays should be pharmaceutically acceptable anions and cations as are known in the art. Polar derivative groups can also include OH, esters, amides, polar halogenated alkyl or aryl groups (such as —$CF_3$ or —$C_6F_5$ groups) or halogens.

Functional groups may also include non-charged groups, groups of low polarity or non-polar groups, including among others alkyl groups, (including straight-chain, cyclic or branched alkyl groups), aryl groups, alkyl-substituted aryl groups, heterocyclic groups, heteroaromatic groups, ether groups, polyether groups, polyetheylene glycol moieties or fragments, polyethylene oxide moieties or fragments, thioether groups, as well as alkyl and aryl groups substituted with OH, OR (where R is alkyl or aryl groups), or one or more halogens.

Functional groups which contain carbonyl (—C=O) groups, such as esters, amides and carbamates, —O—CO—R, —CO—$N(R)_2$, —O—CO—$N(R)_2$ where R is an alkyl, alkenyl or aryl group can also exhibit improved solubility. These R groups can also be substituted with charged or polar groups, including CO, OCO, $N(R)_2$, halogen (F, Cl, Br, I) or OH groups. Alkyl and alkenyl groups of substituents can be straight-chain, branched, or cyclic. Preferred alkyl groups that are substituents or that represent portions of substituents have one to 6 carbon atoms, with methyl, ethyl and propyl groups being more preferred. Cyclic alkyl groups are preferably cyclohexyl or cyclopentyl groups. Preferred alkenes have one or two double bonds. Preferred aryl groups that are substituents or that represent portions of substituents contain one or two aromatic rings which are typically 5- or 6-member rings and which may be heterocyclic. Preferred aryl groups include optionally substituted phenyl groups which may be substituted with polar or charged (e.g., halogen, —$COO^-$, or —COOR groups). However, preferred non-charged substituents are generally selected to increase solubility of and minimize aggregation of the fullerene or endohedral fullerene and are compatible with other substituents, particularly the charged substituents, and with the intended use of the fullerene or endohedral fullerene.

Derivatized fullerenes and endohedral fullerenes of this invention may carry functional groups that enhance absorption in target tissues by attaching at least one functional group to the fullerene cage that functions for targeting tissue, e.g. is a chemical or biological species that selectively binds to or accumulates in certain cell or tissue types. Biological species useful for such targeting are known in the art and can be readily attached to the fullerene. Biological species include, among others, steroid and other ligands for cell surface receptors; antibodies (or fragments thereof), peptides, proteins (or fragments thereof), and nucleic acids. Derivatized fullerenes and endohedral fullerenes of this invention may carry functional groups that function as reporter (moieties whose presence is qualitatively or quantitatively detectable by some means, such as a radiolabel, or fluorescent or phosphorescent labels).

A single cycloalkyl or heterocycloalkyl group which may be substituted with various charged, polar, hydrophilic or non-polar groups (particularly those specifically listed herein) can be added across a double bond of the fullerene via a cycloaddition or other reaction. A plurality of such cyclo additions can be performed in a given fullerene. More specifically three, five, six or seven member cycloalkyl or heterocycloalkyl rings can be added across a double bond of the fullerene. These cycloalkyl rings can be substituted with polar, hydrophilic, non-polar or charged groups. Heterocycloalkyl rings may contain a charged species, such as a ammonium ion or quaternary ammonium ion, or they may be substituted with polar, hydrophilic, charged or non-polar groups.

Functional groups can be substituted directly on the fullerene ring or generally more preferably through the well-known Bingel reaction via cyclopropanation of a fullerene double bond. In the later case, up to two non-hydrogen substituents ($X_1$ and $X_2$) can be added to the fullerene double bond by each cyclopropanation resulting in the formation of the derivatized cyclopropane ring on the fullerene e.g.

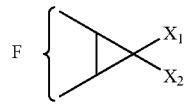

$X_1$ and $X_2$ are selected from the various functional groups listed above. At least two of the total number of $X_1$ and $X_2$ groups on the fullerene are charged groups with like charge. Preferably, the two charged groups are on different cyclopropanation sites on the fullerene. Derivatives of fullerenes and endohedral metallofullerenes include those in which X1 and X2 groups are selected as described above for functional groups or substituents on the fullerene surface. Derivatives of fullerenes and endohedral metallofullerenes include those in which one of $X_1$ or $X_2$ at a cyclopropanation site on the fullerene is a charged group, where all charged groups on the fullerene cage are preferably of like sign. Derivatives of fullerenes and endohedral metallofullerenes also include those in which all of the $X_1$ and $X_2$ groups on the fullerene cage are charged groups.

Water-soluble derivatives of this invention include those where the fullerene has the structure:

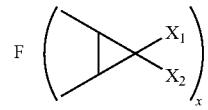

where F is the fullerene and $X_1$ and $X_2$ are functional groups and x is the number of cyclopropyl groups on the fullerene 39. In specific embodiments, x is 5 or more and at least two of the $X_1$ and $X_2$ functional groups are charged groups. In other specific embodiments all of the $X_1$ and $X_2$ functional groups are charged groups. In other specific embodiments x is 4, 5, 6, 7, 8, 9, 10, 11 or 12.

In specific embodiments the derivatization methods herein provide water-soluble endohedral metallofullerenes which exhibit minimal aggregation or improved biodistribution. In preferred embodiments the methods herein are used to generate water-soluble endohedral metallofullerenes derivatized with a plurality (two or more) of functional groups (or substituents) wherein at least two of the plurality of functional groups (or substituents) are charged groups (either both anionic or both cationic) under the conditions in which they will be employed, e.g., at physiologic pH.

Functional groups useful in this invention can be selected from the groups >CR$_1$R$_2$ and >SiR$_1$R$_2$ where R$_1$ and R$_2$ are organic groups independently selected from the group consisting of optionally substituted aryl groups, —COOR$_3$, —O—CO—R$_3$, —CO—NR$_3$R$_4$, —COR$_3$, —CN, —P(O)(OR$_3$)$_2$, SO$_2$R$_3$, -and O—CO—N R$_3$R$_4$ where R$_3$ and R$_4$ are independently selected from hydrogen, an aryl group, an alkyl group, or an alkenyl group each of which may be substituted with one or more substituents selected from the group consisting of —CO—, —OCO—, and —N(R$_5$)$_2$, where R$_5$ is hydrogen, an aryl group, an alkyl group, or an alkenyl group.

In preferred embodiments the number of functional groups and the number of those groups that are charged on the endohedral metallofullerene increases with increasing size of the fullerene cage. Generally, for endohedral metallofullerenes of formula M@C$_{2n}$, it is preferred that at least about ⅙ of the double bonds on the fullerene cage carry at least one non-hydrogen functional group and that at least about ⅓ of these functional groups are charged groups. In more preferred embodiments, at least about ⅓ of the double bonds on the fullerene cage carry at least one non-hydrogen functional groups. In other more preferred embodiments, at least about ½ of the non-hydrogen functional groups on the fullerene are charged groups. In specific embodiments, all of the functional groups on the endohedral metallofullerene are charged groups. Non-charged functional groups may be selected to be polar and/or hydrophilic to enhance solubility of the endohedral fullerene in water. Non-charged functional groups or substituents can be selected generally from polar groups and groups of low polarity and non-polar groups as noted in the various groups above.

In specific embodiments, the methods herein can be employed to produce endohedral metallofullerene derivatives having a mixture of carboxylate and hydroxy groups, preferably those having at least two carboxylate anion groups (present as carboxylic acid groups or carboxylate salts) and a sufficient number of OH groups to ensure water-solubility of the metallofullerene. Water soluble endohedral metallofullerenes carrying two or more carboxylate groups in combination with one, two three or more OH substituent groups can exhibit improved solubility, reduced aggregation and or favorable biodistribution.

In specific embodiments, the methods herein can be employed to produce endohedral metallofullerene derivatives having two or more carboxylate substituents. Carboxy-substituted endohedral metallofullerenes include those in which at least about ⅙ of the double bonds of the fullerene are derivatized with at least one carboxyl group. In preferred embodiments, carboxy-substituted endohedral metallofullerenes include those in which at least about ⅙ of the double bonds of the fullerene are derivatized with two carboxyl group. Carboxy-substituted endohedral metallofullerenes include those in which at least about ⅓ of the double bonds of the fullerene are derivatized with at least one carboxyl group. In preferred embodiments, carboxy-substituted endohedral metallofullerenes include those in which at least about ⅓ of the double bonds of the fullerene are derivatized with two carboxyl groups.

In a more specific embodiment, M@C$_{2n}$(C(COO$^-$A$^+$)$_2$)$_x$ or M@C$_{2n}$ (C(COO$^-$)$_2$B$^{2+}$)$_x$ compounds are provided wherein 2n can be about 50 or more and the value of x can vary from 1 to about 10, or x can be greater than 10, particularly for 2n greater than 60. A in the formula can be any monocation and B any dication, particularly pharmaceutically acceptable cations, and can include anions of alkali metals (Li, Na, K, Rb and Cs). Other cations can include alkaline earth metals or organic-based cations, such as quaternary ammonium cations and other substituted ammonium species, including amino acid residues. M in the formula can generally be any metal ion, but in particular embodiments is a lanthanide metal ion for use in medical imaging technologies, particularly non-RES MRI imaging, and specifically M is a Gd ion. Carboxy-substituted M@C$_{2n}$ may be further derivatized with one or more polar and/or hydrophilic groups (e.g., OH or halogens) and/or derivatized with one or more biological species for targeting and/or derivatized with one or more reporter groups.

In a yet more specific embodiments the invention provides methods for making water-soluble endohedral metallofullerenes exhibiting improved biodistribution having the structures M@C$_{2n}$(C(COO$^-$A$^+$)$_2$)$_x$ or M@C$_{2n}$ (C(COO$^-$)$_2$B$^{2+}$)$_x$ where 2n is 60 or more, where x ranges from 4 to about 12, and more preferably is 5 to 10 and yet more preferably is 8 to 10; A is a monovalent cation (or two A's can be a divalent cation) and M is a metal ion, particularly a lanthanide, or a transition metal. In a specific embodiment, M@C$_{60}$(C(COOA)$_2$)$_x$, where M is Gd$^{3+}$ and x and A are as defined above, are particularly useful as MRI contrast reagents. Carboxy-substituted M@C$_{2n}$ may be further derivatized with one or more polar and/or hydrophilic groups (e.g., OH or halogens) and/or derivatized with one or more biological species for targeting and/or derivatized with one or more reporter groups.

In general, the fullerene surface is covered with enough ionized groups, such as those described above, to break apart and prevent inter-fullerene bonding or aggregation. The highly ionized groups can also provide ready linking points for further derivatization. For example, organic groups can be attached via the carboxylate functionalities to increase binding with serum protein components, such as albumin, to raise the blood residency time of the compound and make it a more effective blood pool contrast agent. Other targeting groups can be used including, but not limited to, peptides, polypeptides, proteins, and protein fragments, antibodies and antibody fragments, etc.

Additionally, metallofullerene derivatives containing multiple non-ionizing groups that are extremely soluble in water can also have favorable biodistribution. Non-ionizing groups useful for the invention include serinol amide (—NHC(CH$_2$OH)$_2$), serinol amide derivatives such as —C(NHC(CH$_2$OH)$_2$)$_2$, polyethylene glycol moieties or fragments, polyethylene oxide moieties or fragments. Sufficient numbers of these groups may be employed to prevent inter-fullerene aggregation. These highly water-soluble, but non-ionized groups can be combined with one or preferably two or more charged functional groups to obtain water-soluble fullerene derivatives with improved biodistribution.

Scheme 1 provides representative examples of derivatized fullerene structures of this invention. Note that fullerenes that can be derivatized by the methods of this invention, include among others, empty or endohedral fullerenes, carbon nanotubes, carbon coated nanoparticles and metal-carbon nanoencapsulates. These fullerenes can be derivatized with any one or more of the groups as listed above or as illustrated Scheme 1.

The invention further relates to method for using water-soluble fullerenes and endohedral metallofullerenes made by the methods of this invention and which exhibit minimal or non-aggregation in various therapeutic and diagnostic applications and particularly as MRI contrast agents.

BRIEF DESCRIPTION OF THE DRAWINGS

FIG. 1. is a positive-ion LD-TOF mass spectrum of the "Gd@$C_{60}$ class" of fullerenes; inset is an expansion of the 870 to 900 mass region, showing the isotope patterns for Gd@$C_{60}$ and the empty fullerene, $C_{74}$.

FIG. 2. is a positive-ion MALDI-TOF mass spectrum of the Gd@$C_{60}$[C(COOCH$_2$CH$_3$)$_2$]$_{10}$ derivative product ($S_8$ matrix); x=10 derivative groups corresponds to the parent peak, with the lesser x peaks due to molecular fragments formed by the laser desorption process.

FIG. 3. Representative in vivo MRI intensity-derived biodistribution data showing the Gd@$C_{60}$[C(COOH)$_2$]$_{10}$ signal enhancement within the first five minutes of administration, revealing rapid renal uptake with a minimum of liver uptake (red filled circles, kidney; blue filled squares, liver).

FIG. 4. Representative in vivo rodent MR images focusing on a cross section containing a portion of one kidney. a, baseline image without contrast agent; b, image of the same cross section 16 min after administration of Gd@$C_{60}$[C(COOH)$_2$]$_{10}$ with increased signal intensity in the kidney.

DETAILED DESCRIPTION OF THE INVENTION

The term "fullerene" is used generally herein to refer to any closed cage carbon compound containing both six- and five-member carbon rings independent of size and is intended to include the abundant lower molecular weight $C_{60}$ and $C_{70}$ fullerenes, larger known fullerenes including $C_{76}$, $C_{78}$, $C_{84}$ and higher molecular weight fullerenes $C_{2N}$ where N is 50 or more (giant fullerenes) and which may optionally be nested and/or multi-concentric fullerenes. The term is intended to include "solvent extractable fullerenes" as that term is understood in the art (generally including the lower molecular weight fullerenes that are soluble in toluene or xylene) and to include higher molecular weight fullerenes that cannot be extracted, including giant fullerenes which can be at least as large as $C_{400}$. Additional classes of fullerenes include, among others specifically noted herein, endohedral fullerenes contains one or more elements, particularly one or more metal elements, and heterofullerenes in which one or more carbons of the fullerene cage are substituted with a non-carbon element, such as B or N. The term fullerenic material is used generally to refer to a material that contains a mixture of fullerenes or a mixture of one or more fullerenes with non-fullerenes, e.g., amorphous carbonaceous materials that may for example be formed during fullerene synthesis by any known method and includes raw or crude preparations of fullerenes, such as combustion soot as well as raw or crude preparations of fullerenes that have been at least partially purified, for example, by extraction and/or sublimation.

Fullerenes are members of a broader class of materials called "carbon nanomaterials" which as used herein generally refers to any substantially carbon material containing six-membered rings that exhibits curving of the graphite planes, generally by including five-membered rings amongst the hexagons formed by the positions of the carbon atoms, and has at least one dimension on the order of nanometers. Examples of carbon nanomaterials include, but are not limited to, fullerenes, single-walled carbon nanotubes (SWNTs), multiple-walled carbon nanotubes (MWNTs), nanotubules, and nested carbon structures with dimensions on the order of nanometers. Carbon nanomaterials may be produced in soot and, in certain cases, carbon nanomaterials may be isolated from the soot or enriched in the soot. Soot produced during the synthesis of carbon nanomaterials, such as fullerenes, typically contains a mixture of carbon nanomaterials which is a source for further purification or enrichment of carbon nanomaterials or which may itself exhibit desired properties of carbon nanomaterials and be useful as an addition to convey those properties. The term "carbon nanomaterials," when used without limitation, is intended to include soot containing detectable amounts of carbon nanomaterials. For example, the term fullerenic soot is used in the art to refer to soot containing fullerenes. Fullerenic soot is encompassed by the term carbon nanomaterials. Non-fullerenic carbonaceous materials include, but are not limited to, non-fullerenic carbon nanomaterials as well as amorphous carbonaceous materials. Carbon nanomaterials are not amorphous carbonaceous materials.

Fullerene and endofullerene derivatives of this invention useful in therapeutic and diagnostic applications are water-soluble. In general, derivatives employed in therapeutic applications are sufficiently water-soluble so that a therapeutically effective amount of the derivatives fullerene or endofullerene can be delivered to a patient and provide a therapeutic benefit. The absolute level of water-solubility needed to obtain a therapeutic effect will then depend upon the therapeutic effectiveness of the derivative. In preferred embodiments, derivatized fullerenes and endofullerenes of this invention exhibit water-solubility of greater than about 0.1 mM. In more preferred embodiments derivatized fullerenes and endofullerenes of this invention exhibit water-solubility of greater than about 1 mM. In yet more preferred embodiments derivatized fullerenes and endofullerenes of this invention exhibit water-solubility equal to or greater than about 3 mM. Derivatization of fullerenes or endohedral fullerenes with a plurality of charged, polar or hydrophilic groups generally renders the derivative water-soluble. In general, larger numbers of such groups are needed to achieve a desired level of water-solubility for fullerenes or endofullerenes of larger cage size. Solubility of a given derivative in a given solvent, particularly water or an aqueous solution, can be quantitatively determined using methods known in the art. The term water-soluble as used herein refers also to solubility in aqueous solutions and in particular to aqueous solutions at physiological pH. Quantitative solubility of a derivative in water may be different than its solubility in an aqueous solution.

Biodistribution refers to the distribution of an agent administered to an individual in the tissues, body fluids and organs of that individual (animal or human) after administration. Biodistribution patterns reflecting relative amounts of the agent in different tissues, organs or fluids can be determined using various methods known in the art, and as illustrated in the examples herein. Biodistribution patterns change as a function of time after administration and may exhibit initial accumulation in certain tissues (organs or fluids) followed by decreasing levels due to transfer to other sites or metabolism and/or excretion of the agent. The agent may selectively accumulate in certain tissue and not in other tissue. The agent administered may be a therapeutic or diagnostic agent and dependent upon the application of the therapeutic or diagnostic agent a given biodistribution pattern over time, may be more or less desirable for that application. For example, in certain therapeutic applications it is desirable to target the therapeutic agent to given tissue, e.g. cancer tissue. Methods are known in the art for achieving such targeting by functionalization of an agent with tissue selective or cell selective functional groups (e.g., those exhibiting having cell surface binding function.) Similar, it may be beneficial to target diagnostic agents to certain tissue types, e.g., to selectively enhance imaging. Notwithstanding the specific benefits of such selective targeting of therapeutic and diagnostic agents, it is generally not beneficial for a therapeutic agent or particularly for a diagnostic agent to accumulate in tissues or organs over extended periods of time (days, months or years). It is generally beneficial for a therapeutic agent or diagnostic agent to be metabolized and/or excreted from an individual in a reasonably rapid manner and avoid excessive accumulation, particularly in the liver, spleen, lymph nodes or bone marrow (the RES tissues.) Undesired accumulation is a more significant problem for therapeutic agents and diagnostic agents that are not metabolized or are only slowly metabolized in vivo. It is most often beneficial for therapeutics and diagnostic agents, particularly those like fullerenes which may not be readily metabolized, to be passed to the kidneys for excretion in urine. One mechanism which enhances accumulation of agents in certain tissues is uptake by the RES system which results generally in accumulation of agents in RES tissue, particularly the liver. As noted above, fullerenes can aggregate in aqueous media and such aggregates will exhibit higher levels of uptake by the RES system and as a result will accumulate in RES tissues.

Fullerene and endohedral fullerene derivatives of this invention exhibit improved biodistribution in that they exhibit relatively low levels of in vivo up take into RES tissue as demonstrated by uptake levels into the liver in the short term (minutes or hours) after administration to an individual. The levels of in vivo uptake into RES tissue by fullerene and endohedral fullerene derivatives of this invention are generally lower than those of in vivo uptake into RES tissue in comparable in vivo systems observed for underivatized fullerenes (e.g., $C_{60}$), monosubstituted $C_{60}$ (e.g., $C_{60}$—N-dimethylpyrrolidine ammonium iodide of Bullard-Dillard et al., 1996, or compounds 1 and 2) or polyhydroxylated water-soluble fullerenes (particularly polyhydroxylated $C_{60}$). Fullerene and endohedral fullerene derivatives of this invention also exhibit improved biodistribution in that they exhibit relatively rapid excretion from the individual (e.g., via the kidney) in the short term (minutes or hours) after administration. The excretion rates of fullerene and endohedral fullerene derivatives of this invention are faster and preferably at least about 50% faster than those observed in comparable in vivo systems for underivatized fullerenes (e.g., $C_{60}$), monosubstituted $C_{60}$ (e.g., $C_{60}$—N-dimethylpyrrolidine ammonium iodide (Bullard-Dillard et al., 1996) or compounds 1 and 2), or polyhydrolylated water-soluble fullerenes (particularly polyhydroxylated $C_{60}$. Biodistribution and rates of excretion can also be assessed by tissue distribution experiments and plasma clearance studies in vivo as known in the art and as described in Bullard-Dillard et al., 1996. Biodistribution may also be assessed using absorption, distribution, and excretion experiments as exemplified and illustrated in Yamago et al., 1995.

Fullerene and endofullerene derivatives of this invention useful in therapeutic and diagnostic applications contain at least two charged functional groups, preferably carboxyl groups, and as a result exhibit biodistribution characterized by generally lower uptake levels in vivo by RES tissues. More specifically, fullerene and endofullerene derivatives of this invention exhibit biodistribution characterized by lower uptake levels in vivo by RES tissues than uptake levels by RES tissues of underivatized fullerenes and endofullerenes as well as water-soluble fullerene and endofullerene derivatives that do not have two or more charged functional groups. The presence of charged functional groups on the fullerene or endohedral fullerene is believed to sufficiently minimize fullerene aggregation in water or aqueous solution to minimize or avoid uptake of the derivatized fullerene or endofullerene by the RES.

In a preferred embodiment the number of charged groups (starting with a minimum of two charged groups) on the fullerene or endohedral fullerene which provides for improved biodistribution and limits aggregation increases generally with the size of the fullerene cage as noted above. In more preferred embodiments, the fullerene or endohedral fullerene is derivatized with three or more charged groups, four or more charged groups, six or more charged groups, eight or more charged groups, ten or more charged groups, twelve or more charged groups, fourteen or more charged groups, sixteen or more charged groups, eighteen or more charged groups or twenty or more charged groups. In general, more preferred derivatized fullerenes of this invention are those that have the most charged functional groups.

The derivatization methods of this invention allow the production of water-soluble derivatives of fullerene and metallofullerene therapeutics or diagnostics which retain therapeutic activity or retain usefulness for diagnostics and which exhibit improved biodistribution, in particular which exhibit lower levels of in vivo uptake by the RES compared to the fullerene or metallofullerene therapeutic or diagnostic prior to derivatization. In preferred embodiments, the derivatization methods herein provide water-soluble fullerene or metallofullerene derivatives which exhibit improved biodistribution without any significant loss of therapeutic effectiveness compared to the therapeutic fullerene or metallofullerene prior to derivatization. In other preferred embodiments, the derivatization methods herein provide water-soluble fullerene or metallofullerene derivatives which exhibit improved biodistribution and increased water-solubility without any significant loss of therapeutic effectiveness compared to the therapeutic fullerene or metallofullerene prior to derivatization. In other preferred embodiments, the derivatization methods herein provide water-soluble fullerene or metallofullerene derivatives which exhibit improved biodistribution without any significant loss of usefulness as a diagnostic agent compared to the diagnostic fullerene or metallofullerene prior to derivatization. In other preferred embodiments, the derivatization methods herein provide water-soluble fullerene or metallofullerene derivatives which exhibit improved biodistribution and increased water-solubility without any significant loss of usefulness as a diagnostic agent compared to the diagnostic fullerene or metallofullerene prior to derivatization. In derivatization methods used to produce improved therapeutic fullerenes or metallofullerenes, the starting point of derivatization is the therapeutic or diagnostic fullerene or metallofullerene (which may already carry substituents) or the corresponding underivatized fullerene or metallofullerene therapeutic or diagnostic agent. For example, a hydroxylated $C_{60}$ may be derivatized to contain two or more carboxyl groups to generate an improved therapeutic or underivatized $C_{60}$ may be hydroxylated an derivatized to contain two or more carboxyl groups to generate the improved therapeutic. In another example, a hydroxylated $M@C_{60}$ which can be employed as an MRI contrast reagent can be derivatized by addition of two or more carboxyl groups to generate an improved MRI contrast reagent. Alternatively, $M@C_{60}$ may be derivatized to contain two or more carboxyl groups and further derivatized to contain hydroxyl groups to provide the same improved MRI contrast agent. The method of this invention for generating improved therapeutic fullerenes and metallofullerenes can be applied to improve biodistribution or to improve biodistribution and increase water-solubility in any fullerene or metallofullerene that exhibits a therapeutic activity. The method of this invention can be applied to make fullerene or metallofullerene diagnostic agents with improved biodistribution or improved biodistribution and increased water-solubility compared to underivatized fullerene or metallofullerene diagnostic agents.

The present invention generally provides improved methods for treatment with fullerene or metallofullerene therapeutic compounds wherein a therapeutically effective amount of a water-soluble derivative of the fullerene or metallofullerene therapeutic compound which derivative exhibits significantly less uptake in vivo by the RES compared to the therapeutic fullerene or metallofullerene is administered to a patient in place of the fullerene or metallofullerene therapeutic. The water-soluble derivatized fullerene or metallofullerene exhibits improved biodistribution patterns but substantially retains the therapeutic activity of the therapeutic fullerene or metallofullerene. In a preferred embodiment, the water-soluble derivative of the fullerene or metallofullerene therapeutic exhibits ½ or less uptake in vivo by the RES compared to uptake of the fullerene or metallofullerene therapeutic in vivo by the RES. In a more preferred embodiment, the water-soluble fullerene or metallofullerene derivative exhibits 10% or less uptake in vivo in the RES system. In a most preferred embodiment, the water-soluble fullerene or metallofullerene derivative exhibits no substantially uptake in vivo by the RES system (i.e., 5% or less). Uptake in vivo by the RES is assessed by animal model studies employing an animal model appropriate for the mode of administration of the therapeutic, the condition or disorder being treated and the patient (animal or human) being treated. Preferred water-soluble derivatives of the fullerene or metallofullerene therapeutic with improved biodistribution exhibit are at least about 10% as effective as the therapeutic fullerene or metallofullerene before derivatization for the treatment of a given condition or disorder. More preferred water-soluble derivatives of the fullerene or metallofullerene therapeutic with improved biodistribution are at least about as effective as the therapeutic fullerene or metallofullerene before derivatization for the treatment of a given condition or disorder. Therapeutic effectiveness can be assessed by any method that allows quantitative comparison, e.g., relative dosage levels required, relative speed of effect, relative magnitude of effect, etc. More preferred water-soluble derivatives of the fullerene or metallofullerene are at least as water-soluble as the fullerene or metallofullerene therapeutic prior to derivatization and preferably are more water-soluble.

The improved therapeutic fullerenes and metallofullerenes of this invention can be employed to treat various disorders and conditions. For therapeutic applications and methods any known method for administration of the therapeutic appropriate for the condition or disorder being treated and appropriate for the patient being treated can be employed. The fullerenes and metallofullerenes of the invention may be formulated as is known in the art for oral, buccal, parenteral, topical or rectal administration. In particular, the improved derivatized fullerenes and metallofullerenes herein may be formulated for injection or for infusion and may be presented in unit dose form or in multidose containers.

Therapeutic compositions may take such forms as suspensions, solutions, or emulsions in oily or aqueous vehicles, and may contain formulatory agents such as suspending, stabilizing and/or dispersing agents. Alternatively, the active ingredient may be in powder or other solid form for constitution with a suitable vehicle, e.g. sterile, pyrogen-free water, before use.

Therapeutic compositions containing improved fullerene or metallofullerene therapeutics of the invention may also contain other active ingredients, such as antimicrobial agents, or preservatives. In general, therapeutic compositions of this invention can contain from 0.001-99% (by weight) of one or more improved fullerene or metallofullerene therapeutic compounds. The daily dosage employed for treatment of a given patient will be adjusted as known in the art for the clinical condition, age, sex and weight of the patient, and for the type of administration. The daily dosage for administration to an adult patient will typically range from about 1.5 mg/kg to about 1500 mg/kg.

Therapeutics can be formulated in dosage units which are discrete pharmaceutical units, for example, as tablets, dragees, capsules, caplets, pills, suppositories or ampules (containing a defined amount of a liquid or suspension). The active compound content of each unit is a fraction or a multiple of an individual dose. An individual dose preferably contains the amount of active compound which is given in one administration and which usually corresponds to a whole, one half, one third or one quarter of a daily dose. The magnitude of a prophylactic or therapeutic dose of a particular multivalent ligand will, of course, vary with the nature of the severity of the condition to be treated, the particular derivatized fullerene or metallofullerene and its route of administration. It will also vary according to the age, weight and response of the individual patient.

As the term is used herein an effective amount of a given therapeutic to be administered is the amount to be administered to a given patient, over a given time, to effectively treat a given disorder or condition. A disorder or conditions is effectively treated if a measurable improvement in the disorder or condition is observed over a reasonable period of treatment. Those of ordinary skill in the art understand how to determine, employing methods known in the art and without undue experimentation, the effective amount of a given therapeutic to administer to a given patient to treat a given disorder or condition.

Therapeutic formulations of improved fullerene and metallofullerene derivatives of this invention are prepared by known procedures using well-known and readily available ingredients. In making such formulations of the present invention, the active ingredient will usually be mixed with a pharmaceutically acceptable carrier, or diluted by the carrier, dissolved in the carrier or enclosed within the carrier which may be in the form of a capsule, sachet, paper or other container. When the carrier serves as a diluent, it may be a solid, semi-solid or liquid material which acts as a vehicle, excipient or medium for the active ingredient.

The therapeutic compositions of this invention can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, aqueous solutions, syrup, methyl cellulose, methyl and propylhydroxybenzoates, talc, magnesium stearate and mineral oil. The formulations can additionally include lubricating agents, wetting agents, buffering agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

Therapeutic compositions can be formulated using any appropriate solvent or carrier system which may be an aqueous solution, a lyophilized or a spray-dried material so long as desired function is maintained.

In a specific embodiment, derivatized metallofullerenes of this invention exhibiting improved biodistribution are employed as carriers for introduction of therapeutic metals, such as therapeutic radionuclides. Formulation and administration of endohedral metallofullerenes containing medically effective radionuclides, particularly for cancer treatment and other nuclear medicine application is performed by methods well-known in the art.

The derivatized fullerenes and metallofullerenes of this invention with improved biodistribution or with improved biodistribution and solubility can be employed as diagnostic agents and particularly as iii vivo diagnostic agents in which a pharmaceutically acceptable composition containing one or more of the improved derivatized fullerenes or metallofullerenes is administered to a patient for, among others, tissue imaging, tumor imaging or scanning, tissue or organ scanning, or tracing studies. Derivatized metallofullerenes of this invention are of particular use as MRI contrast agents.

In vivo diagnostic agents are formulated using conventional techniques well-known in the art. Formulations, types of carriers and additives will be generally similar to those employed in therapeutic applications. Various modes of administration can be employed and will generally depend upon the type of diagnostic application. An amount of the diagnostic agent sufficient to provide the diagnostic function or benefit desired must be administered to the patient undergoing the diagnostic test. Those of ordinary skill in the art can readily determine with undue experimentation using methods well-known in the art the amount of a given diagnostic derivative of this invention that is needed to carry out a given diagnostic assay. The amount employed will generally be dependent the type of assay, the mode of administration, and the function of the diagnostic agent (tracer, contrast agent, etc.). The amount of MRI contrast agent employed can be generally determined for a given application in view of $r_1$ values or other properties that can be readily determined for a given agent. The amount of in vivo diagnostic agent administered must also be appropriate for the condition, age, sex, and weight of the patient.

It will be appreciated by those in the art that it may not be possible due to steric constraints, the type of reaction being employed or changes in reactivity with increasing functionalization to derivatize all available sites on the fullerene cage. The maximum number of functional groups that can be attached to a given fullerene cage will depend upon the size of the fullerene cage as well as upon the size and chemical nature of the functional group or groups that are to be attached and in most cases will be less than the number of available sites for derivatization. In general, it is possible to attached a larger number of sterically smaller functional groups to a given fullerene cage than sterically larger functional groups. It will further be recognized that due in general to the large number of possible derivatization sites on a fullerene a mixture of derivatives which may contain different numbers of functional groups or different isomers is most often generated during reactions. Fullerene and endohedral fullerene derivatives prepared by the methods herein will typically be prepared as mixtures, preferably the desired derivative exhibiting desired improved solubility or biodistribution is the major component of the mixture. Methods are available in the art for enhancing the amount of a desired fullerene derivative in a mixture, in particular derivatives exhibiting differential solubility properties can often be separated. However, application of such methods may not be needed to achieve the desired beneficial effect of derivatization. Often a mixture of derivatives can be employed without significant detrimental effect.

As used herein, "derivatization" generally refers to the chemical modification of a fullerene or the further chemical modification of an already derivatized fullerene. Derivatization of a fullerene refers to the attachment, typically via covalent bonds, of one or more chemical groups to the fullerene surface. Further derivatization of a derivatized fullerene refers to further attachment of groups to the fullerene surface.

The methods of this invention can employ various procedures, methods and techniques known in the art for introducing functional groups onto the fullerene cage of fullerenes or metallofullerenes. Hirsch, A., 1994 and Wilson et al. 2000a provide reviews of fullerene chemistry including methods for derivatization of fullerenes and metallofullerenes. U.S. Pat. Nos. 6,162,926 and 6,399,785 and references therein provide a number of methods for the derivatization of fullerenes. Methods described, exemplified and referenced in these patents can be employed in the derivatization methods of this invention. Methods that can be applied to fullerene cage derivatization useful in the methods of this invention include among others:

1. Cycloadditions
   Diels-Alder [4+2] cycloadditions
   [3+2] cycloadditions
   Oxidative [3+2] cycloadditions
   Addition of azides
   Addition of diazomethanes, diazoacetates, diazoamides
   Addition of trimethylenemethanes
   Addition of nitrile oxides
   Addition of sulfinimides
   Addition of disiliranes
   Addition of azomethine ylides (fulleropyrrolidine and fulleroproline formation, including the so-called "Prato reaction" conditions)
   [2+2] cycloadditions (photochemical and otherwise)
   [2+1] cycloadditions (addition of carbenes and silylenes)

2. Halogenation and Arylations
   Halogenation, followed by substitution or partial substitution 3. Nucleophilic Additions
   Michael additions and the standard Bingel-Hirsch reaction
   Modified-Bingel addition as described in published US patent 20030065206 A1
   Addition of amines
   Direct addition of nucleophiles (anionic and neutral nucleophiles) (i.e. carbanions, alkoxides, metal-organic intermediates, etc.)

4. Electrophilic Addition
   Addition of strong to very strong electrophiles
   Addition of weak to strong electrophiles to anionic or otherwise electron-rich fullerenes or metallofullerenes 5. Radical Addition (Mono- and Poly-Radical Addition)

6. Addition/Coordination of Organometallic and/or Metal Coordination Complexes (Primarily Transition Metals and Their Complexes.)

Scheme 1 illustrates a number of representative functional groups that can be employed in the methods herein. The carboxylate containing functional groups of compound 1 and 2 (above) can also be employed as charged functional groups in the methods of this invention.

The derivatization method of this invention is based in one embodiment on the cyclopropanation reaction as applied to soluble fullerenes first reported by Bingel et al. and further expanded upon by Hirsch et al. (Bingel, 1993; Hirsch, 1994; U.S. Pat. No. 5,739,376) and as applied to insoluble fullerene as described in U.S. published patent application 20030065206, published Apr. 3, 2003. In the "Bingel derivatization", base-induced deprotonation of α-halo (halogen: F, Cl, Br, I) substituted bis-malonates and more generally alpha-halo-CH-acids (see U.S. Pat. No. 5,739,376) examples of the "cyclopropanation reagent" as used herein produces an incipient carbanion. This nucleophilic carbanion adds to the fullerene surface, making a new carbon-carbon bond, followed by elimination of the halide anion, completing the cyclopropanation and leaving a neutral derivative group positioned 1,2 across a carbon-carbon double bond of the fullerene. The cyclopropanation reagent of the method of this invention can also be generated in situ by treatment of mono- and bis-malonates and other acids and esters, for example, with halogen-releasing agents such as $CBr_4$, $I_2$, etc. (as described by Camps, 1997; Nierengarten, 1997). This allows for derivatization with more elaborately substituted groups for which the α-halo precursor may be difficult to individually prepare and/or isolate as a reagent. The Camps and Nierengarten references are specifically incorporated by reference herein to provide details including useful halogen-releasing agents and esters and acids of in situ generation of cyclopropanation reagents. Other methods known in the art for the generation of cyclopropanation reagents can be employed in the methods of this invention.

It will be appreciated by those in the art that multiple functional groups may be attached to a fullerene cage in a single reaction and that the number of groups attached can generally be controlled by adjusting the reaction conditions employed. When it is desired to derivatized a fullerene with two or more different non-hydrogen functional groups, the order in which the derivation reactions are carried out may affect the outcome of the reactions. In general, one of ordinary skill in the art, in view of the body of teachings in the art concerning fullerene derivatization methods, in view of what is generally known in the art and in view of the teachings herein can employ or readily adapt methods known in the art to prepare the derivatives of this invention.

$M@C_{60}$ and related metallofullerenes are a class of molecules completely insoluble in the usual fullerene solvents (e.g., toluene, xylene). Their insolubility arises from intermolecular polymerization caused, at least in part, by their open-shell electronic configuration and small HOMO-LUMO gaps (Diener and Alford, 1998), Largely because of the insolubility of this class of metallofullerene, much of the previous work with metallofullerenes has instead focused on the soluble $M@C_{82}$ class (Bethune et al. 1993; Nagase et al. 1996; Liu and Sun, 2000; Nagase et al. 2000; Shinohara, 2000). While also having open-shell electronic configurations, the intermolecular association of certain $M@C_{82}$ isomers is apparently much weaker than in the $M@C_{60}$ class because of significant electron density localization of the unpaired electron inside the fullerene cage (Kessler et al., 1997) The reported processes for isolating these soluble $M@C_{82}$ species from the products of arc synthesis are labor-intensive and expensive, relying on multi-step HPLC purification using costly specialty columns (Shinohara et al. 1993; Bethune et al. 1993; Nagase et al. 1996; Liu and Sun, 2000; Nagase et al. 2000; Shinohara, 2000.) In addition, some of the $M@C_{82}$ species are air sensitive. Higher yields of soluble $Sc_3N@C_{80}$ and related endohedral fullerenes have been reported (Stevenson et al., 1999) but their purification still relies on costly and time-consuming HPLC separations of minor components of the arc process. For these reasons, the relatively low availability of metallofullerenes has hampered the advancement of metallofullerene-based applications.

Recently, methods for generating larger quantities of metallofullerene $M@C_{60}$ class materials have been developed as described in commonly owned U.S. provisional application No. 60/326,353, filed Oct. 1, 2001, U.S. patent application Ser. No. 10/263,375, filed Oct. 1, 2002 (published on Apr. 3, 2003 as U.S. 20030065206), and PCT application US/02/31362 filed Oct. 1, 2002. Each of these applications are incorporated by reference in their entirety herein for the teachings provided regarding derivatization of fullerenes and metallofullerenes.

These methods are described herein by reference to the $Gd@C_{60}$ class of endohedral metallofullerenes which are of particular interest for applications as MRI contrast agents. However, the methods described herein can be readily applied by one of ordinary skill in the art to the preparation of other metal-containing fullerenes, and in particular to all $M@C_{60}$, $M@C_{70}$, $M@C_{74}$, in general to all insoluble metallofullerenes that are polymeric/intermolecularly bonded solid, and including endohedral metallofullerenes that contain more than one metal. M is generally any metal, and in particular is any lanthanide, actinide, rare earth or transition metal (including any radioactive metal, magnetic or paramagnetic metal). Additionally, the specific methods exemplified can be applied to empty small-band gap fullerene which are insoluble in common fullerene solvents and to derivatization of giant fullerenes.

$Gd@C_{60}$ was generated by the standard DC arc discharge of $Gd_2O_3$-impregnated graphite rods, using cathode deposit "back-burning" to maximize the total yield of fullerenes per arc run. Sublimation was used to separated the fullerenes (including both soluble and insoluble empty fullerenes and $Gd@C_2$, endohedrals) from the non-fullerene carbon soot (Diener and Alford, 1998; Diener et al., 1997.) Exploiting the insolubility of the $M@C_{60}$ class, the soluble $C_{2n}$ and $Gd@C_{2n}$ fullerenes were removed from the sublimate by repeated o-dichlorobenzene washings, e.g., using a Soxhlet extractor operating at 40 torr and 100° C., until the washings were colorless. The collection of the sublimate and extraction were performed anaerobically due to the air sensitivity of some endohedral fullerene materials (Hettich et al., 1999; Bethune et al., 1993; Nagase et al., 1996; Liu and Sun, 2000; Nagase et al., 2000; Shinohara, 2000.)

Reductive and oxidative treatments of mixed endohedral fullerene materials can be used to separate fractions of fullerenes having similar redox properties from other components with differing redox properties. (Diener and Alford, 1998; U.S. Pat. Nos. 6,517,799 and 6,303,016 and commonly owned U.S. patent application Ser. No. 10/263,374; PCT application US/02/31361, both filed Oct. 1, 2002 and U.S. provisional application No. 60/326,307, filed Oct. 1, 2001 all of which are incorporated by reference herein for their teachings regarding separations of fullerenes.) In the exemplified separation, a chemically oxidative treatment was used to enrich the $Gd@C_{60}$ content of the insoluble material by solubilizing and removing several percent of oxidizable $Gd@C_{2n}$ ($2n \geqq 72$) and $C_{74}$. The remaining insoluble "$Gd@C_{60}$ fraction" of metallofullerenes, the mass spectrum of which is shown in FIG. 1, is composed primarily of $Gd@C_{60}$ and $Gd@C_{74}$, with smaller amounts of $Gd@C_{70}$, empty $C_{74}$, and other minor $Gd@C_{2n}$ species with $2n>70$. Only traces of $C_{60}$, $C_{70}$, etc. remained in this material. Over 500 mg of the Gd@$C_{60}$ fraction was readily obtained from ca. 2.5 g of starting sublimate, using this non-chromatographic separation process. This is a considerably larger amount of material than can be currently obtained by chromatographic separation of only the soluble metallofullerenes, e.g. Gd@$C_{82}$ or the various soluble $M_3N$@$C_{2n}$ species such as $Sc_3N$@$C_{80}$. (Stevenson et al. 1999; Bethune et al., 1993; Nagase et al., 1996; Liu and Sun, 2000; Nagase et al., 200 and Shinohara, 2000.) While Gd@$C_{60}$ has yet to be isolated as a pure material, it is the dominant component (at least about 50%, more typically about 75%) of this class or fraction of fullerene molecules having very similar properties (see FIG. 1).

There are a number of reports of exohedral derivatization of metallofullerenes. Akasaka et al, 1995 (a-c) reported the first derivatizations of La@$C_{82}$, Gd@$C_{82}$, $La_2$@$C_{80}$ and $Sc_2$@$C_{84}$ with disiliranes and digermanes. Suzuki et al., 1995 reported the reaction of La@$C_{82}$ with substituted diazomethanes to form methanofullerene derivatives. Feng et al., 2002 reported generation of methanofullerene derivatives of Tb@$C_{82}$ by Cu(I) catalyzed addition of α-diazocarbonyl compounds. Additionally, several different groups have reported polyhydroxylation of the metallofullerene cages Ho@$C_{82}$, $Ho_2$@$C_{82}$, Pr@$C_{82}$ and Gd@$C_{82}$. See: Wilson et al., 1999; Cagle et al., 1999; Zhang et al., 1997; Mikawa et al., 2001 and Sun et al., 1999. However, these reported derivatizations began with metallofullerenes already soluble in the reaction medium, which in most cases was toluene or a similar "standard" fullerene solvent. In contrast, the process of this invention is highly effective for derivatizing insoluble fullerenes, and specifically the exohedral chemical modifications described herein allow endohedral fullerenes that previously went unused as waste (including M@$C_{60}$) to be utilized.

A cycloaddition reaction widely used to add functionalities across carbon-carbon double bonds of fullerenes is the base-induced Michael addition of malonates first reported for $C_{60}$ by Bingel, 1993 (see also U.S. Pat. No. 5,739,376) and later expanded upon by Hirsch et al., 1994. The reaction conditions described in these references (using hydrocarbon solvents like toluene and sodium hydride or 1,8-diazabicyclo[5.4.0]undec-7-ene (DBU) as the base) are not optimal with metallofullerenes. DBU use is not preferred with metallofullerenes because, like basic nitrogen solvents (pyridine, aniline, dimethylformamide, etc., see Kubozono et al., 1996; Inoue et al., 2000; Kanbara et al., 2001; Ogawa et al., 2000 and Solodovnikov et al., 2001) it adds readily to fullerene surfaces (Skiebe et al., 1994), a problem only exacerbated by the electronegativity of the metallofullerene.

For the Gd@$C_{60}$-fraction metallofullerenes, reaction conditions are employed that derivatize and solubilize the insoluble polymer material without requiring their prior dissolution. Using tetrahydrofuran (THF) as solvent at room temperature with a ca. 15-fold excess of diethyl bromomalonate and alkali metal hydride (NaH or KH), the Gd@$C_{60}$-fraction material is rapidly derivatized with multiple malonate ester groups, which readily solubilize this otherwise intractable material. Other solvents useful for conducting the derivatization reaction include, but are not limited to, at least moderately polar aprotic solvents. Useful solvents specifically include aliphatic ethers, aryl ethers, cyclic ethers, halogenated alkanes (e.g., dichloromethane, tetrachloroethane), halogenated aryls, halogenated benzenes (e.g., ortho-dichlorobenzene, halobenzenes), dialkylsulfoxides (e.g., dimethylsulfoxide) and miscible combinations thereof. Useful ether solvents include tetrahydrofuran, 1,4-dioxane, dimethoxyethane and miscible combinations thereof.

Large amounts of a highly organic-soluble and air-stable derivative can be obtained in only minutes without heating. Mass spectral analysis of the derivatized product (FIG. 2) reveals it to be chiefly composed of Gd@$C_{60}$[C(COO$CH_2CH_3$)$_2$]$_x$, with the parent ion peak at x=10. This ester derivative was readily converted into the water-soluble Gd@$C_{60}$[C(COOH)$_2$]$_{10}$ carboxylate acid using a method reported by Lamparth and Hirsch, 1994 for the conversion of $C_{2n}$[C(COO$CH_2CH_3$)$_2$]$_x$ to the corresponding $C_{2n}$[C(COOH)$_2$]$_x$ species.

The derivatization of M@$C_{60}$ described herein is significant because it provides a solution to the long-standing problem of how to exploit the polymerized M@$C_{60}$ species that, while more abundant than soluble M@$C_{82}$ metallofullerenes, previously went unused. Using more polar solvents like tetrahydrofuran (instead of non-polar hydrocarbons like toluene) in the Bingle-type reaction is believed to facilitate the incipient malonate carbanion to derivatize the solid M@$C_{60}$ surface in an apparently heterogeneous solid/solution phase reaction. In derivatization of Gd@$C_{60}$, the reaction proceeds very rapidly to the deca-addition stage without heating (unlike the traditional Bingel and Hirsch conditions) with the exohedral derivatization breaking up intermolecular polymerization. The derivatization process is easily scalable to produce hundreds of milligram, grams or hundreds of grams of the water-soluble, air-stable M@$C_{60}$[C(COOH)$_2$]$_{10}$ per run.

Measuring the $r_1$ "relaxivity' of a water-soluble paramagnetic compound is a quantitative way to compare its efficacy in relaxing solvent water protons (shortening $T_1$ or the longitudinal relaxation time) to that of other paramagnetic ions and their complexes. (Lauffer, 1987, Caravan, et al., 1999 and Toth et al., 2001) (Note that relaxivity measurement are dependent upon temperature and magnetic field used, so that it is most meaningful to compare $r_1$ values obtained under the same conditions.) Several different groups have identified water-solubilized polyhydroxyl Gd metallofullerene compounds as potential MRI contrast agents, with each reporting different $r_1$ values. Zhang et al. measured $r_1$=47 mM$^{-1}$s$^{-1}$ (at 9.4 T) for a mixed sample of empty fullerene and Gd-metallofullerene polyhydroxyl compounds, while Wilson et al. reported $r_1$=20 mM$^{-1}$s$^{-1}$ for Gd@$C_{82}$(OH)$_x$ (at 0.47 T and 40° C.). More recently, Shinohara and co-workers reported Gd@$C_{82}$(OH)$_x$ (x~40) with an $r_1$ value of 67 mM$^{-1}$s$^{-1}$ (at 0.47 T and 25° C.) and $r_1$=81 mM$^{-1}$s$^{-1}$ (at 1.0 T and 25° C.). These $r_1$ values are all higher than the relaxivities of clinically-used Gd(III) chelates and demonstrate that Gd metallofullerene compounds can serve as potent $T_1$ relaxation agents for water protons.

The relaxivity $r_1$ measured in water for Gd@$C_{60}$[C(COOH)$_2$]$_{10}$ is 4.6 mM$^{-1}$ s$^{-1}$ (at 20 MHz, 40° C. and based on Gd content by ICP analysis). This $r_1$ value is comparable to the best [Gd$^{III}$(chelate)] currently employed commercial MRI contrast agents, such as ProHance™ ([Gd(HP-DO3A)(H$_2$O)] with $r_1$=3.6 mM$^{-1}$s$^{-1}$) and Magnevist™ ([Gd(DTPA)(H$_2$O)]$^{2-}$ with $r_1$=4.3 mM$^{-1}$s$^{-1}$) under similar conditions (Lauffer, 1987; Caravan et al., 1999.) For comparison, La@$C_{60}$[C(COOH)$_2$]$_x$ was prepared in an analogous manner as Gd@$C_{60}$[C(COOH)$_2$]$_{10}$. This La-containing metallofullerene should be similar in electronic structure to its Gd analogue, as both contain trivalent endohedral lanthanide metals (resulting in one unpaired electron on the fullerene cage); however, with its d$^0$ configuration, La$^{3+}$ has no metal-centered unpaired f-electrons. The $r_1$ relaxivity of La@$C_{60}$[C(COOH)$_2$]$_x$ in water was determined to be less than 1 mM$^{-1}$s$^{-1}$ (ca. 0.3 mM$^{-1}$s$^{-1}$ at 20 MHz and 40° C. with x≈10).

Since water molecules have no direct access to a $Gd^{3+}$ ion inside the fullerene carbon cage, it is plausible that an outer sphere relaxation mechanism occurs in these species with water molecules hydrogen-bonded to the water-solubilizing groups on the fullerene surface, with the unpaired f-electrons of the encaged $Gd^{3+}$ ion magnetically coupled to the unpaired electron in the fullerene-centered molecular orbital, which itself transfers some spin density to the substituents. While not wishing to be bound by any particular mechanism, an outer sphere relaxation mechanism is consistent with the large drop-off in relaxivity observed in going from the carboxylated $Gd@C_{60}$ compound (seven f-electrons) to the $La@C_{60}$ analogue (zero f-electrons). Lanthanide metal@$C_{60}$ compounds where the metal has at least one unpaired f electron would be expected to exhibit higher $r_1$ than $La@C_{60}$.

Intermolecularly-aggregated MRI contrast agents are known to exhibit increased rotational correlation times, which results in enhanced relaxivities relative to non-aggregated agents (Toth et al., 2001; Fatin-Rouge et al., 2000.) Thus, the propensity of water-soluble fullerene derivatives to aggregate or clustering in aqueous solution would confuse the interpretation of measured relaxivities. Laser light scattering, small-angle neutron scattering and small-angle X-ray scattering measurements on several water-soluble fullerene derivatives provide experimental evidence for aggregation. Guldi and co-workers have found evidence of aggregation for water-soluble $C_{60}$ derivatives, including $C_{60}(OH)_{18}$ and $C_{60}[C(COOH)_2]$. (See, Guldi et al., 1995; Guldi et al., 1997; Guldi, 1997; and Mohan, et al., 1998.) Pulse radiolysis and triplet lifetime measurements on the $C_{60}$ monoadduct, $C_{60}[C(COOH)_2]$, suggested aggregation in aqueous solution (Guldi et al., 1995 and Guldi, 1997.) Pulse radiolysis and optical absorption spectroscopy with $C_{60}(C_4H_{10}N^+)$ also revealed aggregation for this monoadduct (Guldi et al., 1997 and Guldi, 1997.) Guldi concluded that covalent attachment of only one addend to the $C_{60}$ surface was insufficient to prevent hydrophobic attraction and aggregation of these derivatives. Bensasson et al. reported that lower singlet oxygen quantum yields for $C_{60}[C(COOH)_2]_n$ derivatives (with n=2 to 6) in aqueous solution as compared to the corresponding ethyl esters in toluene was indicative of clustering of the acids in water (Bensasson et al., 2001.)

Furthermore, dynamic light scattering measurements on the polyhydroxyl $C_{60}$ compound $C_{60}(OH)_{18}$ showed evidence for aggregates at high solute concentrations (up to 39 mM) (Mohan et al., 1998.) A small-angle X-ray scattering study reported by Jeng et al., 2001 and Jang et al., 1999 measured $C_{60}(OH)_{18}$ aggregates in aqueous solution of 20 Å $R_g$ ($R_g$=radius of gyration) at 0.7 mM, with the aggregates doubling in size to 40 Å $R_g$ at 50 mM. Water-soluble $C_{60}[(CH_2)_4SO_3Na]_6$ was found to have 19 Å $R_g$ across the range of concentrations from 0.4 to 26 mM in aqueous solution (Jang et al., 2001 and Jang et al., 1999.) Dynamic light scattering measurements on a highly water-soluble dendro-$C_{60}$ monoadduct derivative (having a second generation bis(polyamide) malonate dendrimer with eighteen carboxylate groups) by Brettreich and Hirsch, 1998 revealed clusters of at least two different size ranges. Clusters with average hydrodynamic radii of ca 10 nm and 38 nm were seen at pH=8, with a decrease in size to 5 nm for the smaller clusters at pH=11. Zhou, et al., 2001 recently reported that water-soluble $Ph_5C_{60}K$ forms vesicles having a hydrodynamic radius of 17 nm as detected by laser-light scattering. These different examples demonstrate that intermolecular aggregation of water-soluble fullerene derivatives occurs with a range of different derivative groups having a variety of dispositions on fullerene cages.

Several mechanisms may contribute to the clustering of these water-soluble fullerene derivatives, including both intermolecular hydrogen bonding and hydrophobic fullerene-fullerene attraction with the degree of aggregation varying with concentration. This invention recognizes that the extent of derivatization needed to inhibit or prevent aggregation of fullerenes is dependent on the size of fullerene cage as well as the type of functional group. As noted above, undesired aggregation of fullerenes can be prevented or minimized by derivatization of the fullerene with charged functional groups. Two charged functional groups at a minimum are needed to affect aggregation. Preferred fullerenes exhibiting less aggregation carry three or more charged substituents. Aggregation can be further reduced by functionalization with additional non-charged functional groups (which may be polar, hydrophilic or non-polar). In preferred derivatives at least about ⅙ to ⅓ of the available sites for attachment of functional groups have been derivatized and at least about ⅓ to ½ of the functional groups on the fullerene are charged.

A qualitative assessment of aggregation of water-solubilized $Gd@C_{60}$ compounds by dynamic light scattering (DLS) was performed. DLS measurements comparing polyhydroxylated fullerene compounds such as $Gd@C_{60}(OH)_x$ and $Gd@C_{60}[C(COOH)_2]_{10}$ under the same conditions revealed that the polyhydroxylated fullerenes form aggregates in excess of 100 nm in diameter, while $Gd@C_{60}[C(COOH)_2]_{10}$ displayed no aggregation down to the instrumental detection limit (~10 nm). This order-of-magnitude difference in aggregation propensity correlates with the elevated $r_1$ values seen for the polyhydroxyl compounds in comparison to $Gd@C_{60}[C(COOH)_2]_{10}$. Large clusters of slowly tumbling polyhydroxyl fullerenes will have higher relative relaxivities than comparable molecules that are not intermolecularly aggregated. The deca-methano $Gd@C_{60}$ compound (with its 20 carboxyl groups) exhibits less intermolecular aggregation than the polyhydroxylated fullerenes because of its highly charged surface.

It is further believed that the steric disposition of the ten derivative groups uniformly over the entire surface of the fullerene provides for enhanced protection of the underivatized fullerene surface(s) of $Gd@C_{60}[C(COOH)_2]_{10}$ from hydrophobic-induced aggregation. Thus, the number and type of derivative groups on the fullerene as well as the relative positioning of the groups on the surface affect the extent of intermolecular aggregation. To minimize undesirable aggregation, fullerenes are preferably derivatized with a plurality of functional groups at least two of which are charged groups (under the conditions in which aggregation is to be inhibited (i.e., under physiologic conditions.) Preferably, the substituents are distributed over the entire fullerene or the number of substituents is sufficiently large so that the substituents are distributed over the entire surface.

Aggregation of fullerenes used in in vivo applications is undesirable because it can lead to recognition and uptake of the aggregated fullerene particles by the RES which leads to undesirable biodistribution of the fullerene in RES tissues, such as the liver, and which results in undesired retention of the fullerenes in the body. Derivatization of fullerenes by the methods herein inhibits or prevents undesired aggregation in which particles large enough to be recognized by the RES are formed. It will be appreciated that low levels of aggregation may occur with a given derivative without having a significant detrimental affect on biodistribution or retention of the derivatized fullerene. In general, preferred fullerene derivatives of this invention exhibit no formation of aggregates having diameters of 100 nm or greater in water or aqueous solution (under physiologic conditions). More preferred fullerene derivatives of this invention exhibit no formation of aggregates having diameters of 50 nm or greater in water or aqueous solution (under physiologic conditions). A preferred fullerene derivative of this invention will exhibit no substantial level of aggregation, where no more than about 25 molar % of the fullerene derivatives present are associated in aggregates (in water or aqueous solution under physiologic conditions) with diameters of 10 nm or more. Most preferred fullerene derivatives of this invention will exhibit no formation of aggregates of diameter of 10 nm or greater in water or aqueous solution (under physiologic conditions). Aggregation and the diameters of aggregates formed can be assessed by methods well-known in the art and as exemplified in the examples herein.

Biodistribution of derivatized fullerenes, in particular derivatized metallofullerenes, can be assessed using in vivo MRI experiments. These studies are exemplified by examining the biodistribution of $Gd@C_{60}[C(COOH)_2]_{10}$ in vivo, employing an MR imaging experiment with a rodent model (at an approximate dosage of 35 mg/kg). The MR imaging experiment revealed that $Gd@C_{60}[C(COOH)_2]_{10}$ behaved much like commercially-available Gd chelate-based MRI contrast agents (e.g. Prohance™ and Magnevist™) in this animal model (Wedeking et al., 1990.) Typical biodistribution results are shown in FIGS. 3 and 4. The $Gd@C_{60}[C(COOH)_2]_{10}$ agent moved rapidly to the kidneys, with only minimal uptake into the liver as illustrated graphically in FIG. 3, which compares relative MRI enhancement by the metallofullerene derivative in the kidney vs. the liver in the minutes after injection. FIG. 4 shows examples of the MR images obtained, comparing the MRI intensity of one kidney before contrast agent injection and again 16 min after injection. The lighter color of the kidney in the latter image results from the proton relaxation induced by the paramagnetic $Gd@C_{60}[C(COOH)_2]_{10}$ contrast agent. The agent began undergoing excretion via the bladder within 1 hour of injection. This biodistribution behavior is in striking contrast to that observed in polyhydroxylated fullerene derivatives.

Several complimentary studies on the biodistribution of the polyhydroxylated compounds $^{166}Ho_n@C_{82}(OH)_x$ (n=1, 2; x~16), $Gd@C_{82}(OH)_x$ (x~40) and $^{99m}Tc$-labelled $C_{60}(OH)_x$ have recently revealed high uptake levels of these compounds by the reticuloendothelial system (RES). The radiotracer study conducted by Cagle et al, 1999. with $^{166}Ho_n@C_{82}(OH)_x$ (n=1, 2; x~16) showed significant RES uptake in mice, including concentration in liver and bone. The MR imaging and biodistribution study performed by Mikawa et al., 2001 with $Gd@C_{82}(OH)_x$ (x~40) reported similar results. Qingnuan et al., 2002 have recently published a radiotracer study with the (reportedly non-endohedral) polyhydroxyl $C_{60}$ derivative $^{99m}Tc$—$C_{60}(OH)_x$. The biodistribution results in mice and rabbits also showed significant uptake of the polyhydroxyl fullerene by the kidneys, bone, spleen and liver. The common feature in all in these studies is the polyhydroxyl derivatization of the fullerene cage, while the differences among these compounds (different cage sizes, different endohedral metals or lack thereof, different electronic structures, etc.) apparently do not significantly affect the biodistribution. It also appears that differing degrees of hydroxylation do not produce a major impact on the observed biodistributions. Thus, although derivatization with OH can provide water-soluble fullerenes, OH substituents alone do not function to inhibit aggregation of fullerenes. As provided herein, substitution with a plurality (at least two and preferably more than two) charged substituents is needed to provide significant inhibition of aggregation.

The RES uptake of polyhydroxyl fullerene compounds have important implications for the development of pharmaceuticals based on water-soluble fullerenes. Shinohara and coworkers have noted that polyhydroxyl fullerene compounds induce spontaneous aggregation of erythrocytes when in contact with blood and that addition of mannosyl groups to a polyhydroxyl $C_{60}$ surface diminishes this effect (Kato et al., 2001.) It is not yet clear if in vivo RES uptake stems from intermolecular aggregation causing larger particles to be targeted by the RES or if the RES uptake results from polyhydroxyl fullerene-induced aggregation of erythrocytes (and/or other blood components/proteins), which are then targeted by the RES. A combination of the two actions seems plausible, but one must note that the intermolecular clustering as measured by light scattering techniques and as inferred by relaxivity measurements does not require the presence of blood or blood components to be manifested. For fullerene-based pharmaceuticals to be successful for non-RES targeting, sufficient water solubility without significant RES uptake is required, and the new $Gd@C_{60}[C(COOH)_2]_{10}$ species of this report demonstrates that this goal can be realized for a fullerene-based material.

The following examples further illustrate and exemplify the invention, but are in no way intended to limit the scope of the invention

THE EXAMPLES

General Experimental $Gd(NO_3)_3.6H_2O$ (99.9%) was purchased from Strem Chemicals and used as received. All other chemicals were purchased from Sigma-Aldrich and used as received. Solvents were distilled and dried under inert atmosphere according to standard procedures, except for carbon disulfide, which was used as received. Inert atmosphere manipulations were conducted inside a Vacuum Atmospheres glovebox under argon ($O_2$, $H_2O$<5 ppm). Mass spectrometry was performed with a Bruker Biflex™ III MALDI-TOF MS or with a custom built laser-desorption combination linear and reflectron time-of-flight mass spectrometer, using a sulfur matrix deposited from a carbon disulfide solution when indicated. Fourier-transform infrared spectroscopy was conducted with a Nicolet Magna-IR 550 FTIR spectrometer.

ARC Fullerene Production of Mixed $C_{2N}/GD@C_{2N}$.

$Gd_2O_3$ impregnated graphite rods (¼" diameter Poco Graphite, 40% porosity) doped to a level of ca. 1% Gd were produced according to published procedures (Cagle et al. 1996.) The graphite rods were first evacuated (~1 Torr) then soaked in a saturated absolute ethanolic solution of Gd $(NO_3)_3.6H_2O$ for 30 min. The solution-saturated rods were air dried and then heated in a quartz furnace at ca. 850° C. under vacuum for 3 hours, converting the metal nitrate to the oxide. Gd-containing fullerene soot was generated by the standard direct current (DC) arc-discharge of $Gd_2O_3$-impregnated 6" graphite rods using a custom-built arc apparatus, operating at 150 Torr of helium. Cathode deposit "back-burning" was employed to maximize the yield of fullerenes and metallofullerenes. "Back-burning" (reverse-polarity arcing) consists of periodically briefly reversing the arc polarity so as to arc the solid deposits of material formed on the cathode (relative to the original polarity). Anaerobic sublimation of the raw arc-produced soot[4,18] onto an isolated, water-cooled cold finger inside of the arc chamber at 750° C. separated the fullerenes (a mixture of soluble and insoluble empty fullerenes and $Gd@C_{2n}$ endohedral metallofullerenes) from the non-fullerene carbon soot. Approximately 2.5 g of sublimed fullerenes (the "sublimate") per ten rod arc run was obtained.

Separation of the GD@$C_{60}$ Fraction.

All soluble fullerenes were removed from the anaerobically-collected sublimate by repeatedly washing with o-dichlorobenzene inside the argon-filled glovebox using a continuous-cycling (Soxhlet-style) extractor operating at 40 torr and 100° C., until the washings were colorless. Next, the solids were extracted in dichloromethane suspension with a solution of excess tris(p-bromophenyl)aminium hexachloroantimonate, which solubilized small amounts of oxidizable Gd@$C_{2n}$ species (e.g. Gd@$C_{82}$ and other Gd@$C_{2n}$). The solids were separated from the dark brown filtrate and further treated with aluminum trichloride in o-dichlorobenzene to deplete the amount of $C_{74}$ (U.S. patent application Ser. No. 10/263,374 and PCT application US/02/31361.) The solids were collected by filtration, rinsed with dichloromethane and hexane, and then dried under vacuum. The resulting material was found to be composed of the Gd@$C_{60}$-dominated fraction of fullerenes, including chiefly Gd@$C_{60}$ with smaller amounts of Gd@$C_{70}$, Gd@$C_{74}$, other higher Gd@$C_{2n}$ and $C_{74}$ (with negligible amounts of $C_{60}$ and $C_{70}$).

Derivatization Of GD@$C_{60}$: Synthesis of GD@$C_{60}$[C(COOCH$_2$CH$_3$)$_2$]$_{10}$.

In a typical synthesis of Gd@$C_{60}$[C(COOCH$_2$CH$_3$)$_2$]$_{10}$ (conducted in the glovebox), a suspension of Gd@$C_{60}$ (307 mg, 0.350 mmol) and KH (210 mg, 5.25 mmol) (NaH is an acceptable substitute) was prepared in THF (20 mL) with vigorous stirring (15 min). With continued stirring, diethyl bromomalonate (1.255 g, 5.25 mmol) in THF (~1 mL) was added dropwise to the mixture. Vigorous bubbling was immediately observed (evolution of H$_{2(g)}$) and a dark brown solution color developed within minutes. The mixture was stirred (30 min) after which the dark-brown soluble derivative was separated from excess alkali hydride and small amounts of unreacted fullerene material by filtration (0.45 μm PTFE filter). The product was isolated by THF removal under reduced pressure, was rinsed with hexanes and dried under reduced pressure (yield 331 mg, 41%). FTIR, KBr matrix: C—H aliphatic stretch, 2980, 2927, 2855 cm$^{-1}$; C=O stretch, 1743 cm$^{-1}$.

Conversion of GD@$C_{60}$[C(COOCH$_2$CH$_3$)$_2$]$_{10}$ to GD@$C_{60}$[C(COOH)$_2$]$_{10}$.

Conversion of Gd@$C_{60}$[C(COOCH$_2$CH$_3$)$_2$]$_{10}$ to the water-soluble carboxylate salt Gd@$C_{60}$[C(COOH)$_2$]$_{10}$ was accomplished by reflux in toluene with NaH followed by a methanol quench, according to the method reported by Lamparth and Hirsch for the conversion of $C_{2n}$[C(COOCH$_2$CH$_3$)$_2$]$_x$ to $C_{2n}$[C(COOH)$_2$]$_x$ (Lamparth and Hirsch, 1994; Lamparth et al., 1997.) Lamparth et al., 1997 speculate that this transformation takes place via trace nucleophilic OH$^-$ formed by reaction NaH with trace water in the methanol or by hydrogenolysis of the O-Et bonds. The aqueous-soluble product was converted to the free acid by passage over an acid-form ion-exchange chromatography column (without Gd loss). Next, the solution pH was adjusted to 7.0 with NaOH and the product was dried under reduced pressure at room temperature. FTIR, KBr matrix: O—H, 3425 cm$^{-1}$ (v. broad); C=O asymmetric stretch, 1743 cm$^{-1}$; C=O symmetric stretch, 1146 cm$^{-1}$.

Relaxivity Measurements.

Single-point $r_1$ relaxivity measurements (expressed by the relationship $(1/T_1)_{obsd}=(1/T_1)_d+r_1[solute]$) in aqueous solution were conducted using an IBM PC/20 MiniSpec Relaxometer operating at 40° C. and a fixed field of 0.47 T (20 MHz). All relaxivity data on Gd metallofullerene compounds calculated the $r_1$ values in terms of Gd content, which was independently determined by ICP-AES.

Dynamic Light Scattering (DLS) Measurements.

DLS measurements were performed using a Coulter N4 Plus Dynamic Light Scattering instrument (detection angle 90°) with a lower detection limit of ca. 10 nm in diameter; samples that did not scatter light to a significant degree were judged to not contain particles of sufficient size. DLS measurements in aqueous solution at pH~7 comparing $C_{60}$(OH)$_x$, Gd@$C_{2n}$(OH)$_x$ and Gd@$C_{60}$[C(COOH)$_2$]$_{10}$ species demonstrated aggregation of the polyhydroxylated compounds (having aggregates in excess of 100 nm diameter), but no such aggregation was observed for the polycarboxylated species.

In Vivo MRI Measurements.

To study the MRI contrast and biodistribution behavior of Gd@$C_{60}$[C(COOH)$_2$]$_{10}$ in vivo, an experiment was performed using a Fischer 344 female rat (Sasco, Wilmington, Mass.) weighing 200-220 grams and housed at the Department of Veterinary Medicine and Surgery, University of Texas, M.D. Anderson Cancer Center (Houston, Tex.) with all procedures conforming to institutional guidelines for animal welfare. The rat was injected via the tail vein with 1 mL of a 3 mM solution of Gd@$C_{60}$[C(COOH)$_2$]$_{10}$ in saline at pH=7.4. The dosage was approximately 35 mg/kg, which was well tolerated by the animal. Images were acquired on a 1.5 T GE LX EchoSpeed scanner (GE Medical Systems, Milwaukee, Wis.) using a custom spiral surface coil. The animal was scanned in the prone position in the MRI experiment. Prior to contrast agent administration, coronal flow-compensated $T_1$-weighted fast spin-echo images were acquired from 18 2-mm contiguous sections (echo time of 15 ms, repetition time of 400 ms, echo train length of 2, field-of-view of 12×12 cm, 256×192 matrix, 4 averages). Immediately before, during, and after contrast agent administration, a dynamic fast spin-echo sequence was used to acquire $T_1$-weighted images from 5 2-mm sections (with 2-mm gaps) with a temporal resolution of 11 sec (echo time of 14 ms, repetition time of 400 ms, echo train length of 4, field-of-view of 12×9 cm, 256×128 matrix, 1 average). The total duration of the dynamic scanning sequence was 5 min. Following the dynamic acquisition, fast spin-echo $T_1$-weighted images were acquired from the 18 2-mm contiguous sections (using the parameters listed above) at 10 min, 20 min, 30 min, and 45 min post-contrast agent infusion.

Those of ordinary skill in the art will appreciate that starting materials, reagents, synthetic method, reaction conditions, purification methods, and analytical methods other than those specifically exemplified herein can be employed in the practice of this invention as described herein. Those of ordinary skill in the art will also appreciate that functional equivalents of starting materials, reagents, synthetic method, reaction conditions, purification methods, and analytical methods are known in the art and can be employed, in view of teachings herein and what is well-known in the art, in the practice of this invention without resort to undue experimentation. All art-known equivalents of the starting materials, reagents, synthetic method, reaction conditions, purification methods, and analytical methods exemplified herein are intended to be encompassed by this invention. All reference cited herein are incorporated by reference herein to the extent that they are not inconsistent with the disclosures of this application.

REFERENCES

Advent, A. G., P. Birkett, J. D. Crane, A. D. Darwish, G. J. Langley, H. W. Kroto, R. Taylor, D. R. M. Walton, The structure of $C_{60}Ph_5Cl$ and $C_{60}Ph_5H$ formed via electrophilic Aromatic Substitution, *J. Chem. Soc., Chem. Comm.* 1994: 1463-1464.

Akasaka, T.; Kato, T.; Kobayashi, K.; Nagase, S.; Yamamoto, K.; Funasaka, H.; Takahashi, T. Nature 1995a 374, 600.

Akasaka, T.; Nagase, S.; Kobayashi, K.; Suzuki, T.; Kato, T.; Kikuchi, K.; Achiba, Y.; Yamamoto, K.; Funasaka, H.; Takahashi, T. *Angew. Chem. Intl. Ed. Engl.* 1995b 34, 2139.

Akasaka, T.; Nagase, S.; Kobayashi, K.; Suzuki, T.; Kato, T.; Yamamoto, K.; Funasaka, H.; Takahashi, T. Chem. Comm. 1995c 1343.

Bensasson, R. V.; Berberan-Santos, M. N.; Brettreich, M.; Frederiksen, J.; Göttinger, H.; Hirsch, A.; Land, E. J.; Leach, S.; McGarvey, D. J.; Schönberger, H.; Schröder, C. *Phys. Chem. Chem. Phys.* 2001, 3, 4679.

Bethune, D. S.; Johnson, R. D.; Salem, J. R.; de Vries, M. S.; Yannoni, C. S. Nature 1993, 366, 123.

Bingel, C. Chem. Ber. 1993, 126, 1957.

Brettreich, M.; Hirsch, A. Tet. Lett. 1998, 39, 2731.

Bullard-Dillard, R., K. E. Creek, W. A. Scrivens, J. M. Tour, Tissue Sites of Uptake of 14C-labeled C60, Biorganic Chemistry 24, 376-385 (1996).

Cagle, D. W.; Thrash, T. P.; Alford, M.; Chibante, L. P. F.; Ehrhardt, G. J.; Wilson, L. J. J. Am. Chem. Soc. 1996, 118, 8043.

Cagle, D. W.; Kennel, S. J.; Mirzadeh, S.; Alford, J. M.; Wilson, L. J. Proc. Natl. Acad. Sci USA 1999, 96, 5182.

Camps, X.; Hirsch, A. (1997). "Efficient Cyclopropanation of C60 Starting from Malonates," J. Chem. Soc. Perkin Trans. 1, 1595-1596.

Caravan, P.; Ellison, J. J.; McMurry, T. J.; Lauffer, R. B. Chem. Rev. 1999, 99, 2293.

Chai, Y. Guo, T.; Jin, C.; Haufler, R. E.; Chibante, L. P. F.; Fure, J.; Wang, L.; Alford, J. M.; Smalley, R. E. J. Phys. Chem. 1991, 95, 7564.

Chiang et al. J. Amer. Chem. Soc. 114:10154-10157 (1992).

Diener, M. D.; Smith, C. A.; Veirs, K. D. Chem. Mater. 1997, 9, 1773.

Diener, M. D.; Alford, J. M. Nature 1998, 393, 668.

Dugan, L. L.; Turetsky, D. M.; Du, C.; Lobner, D.; Wheeler, M.; Almli, C. R.; Shen, C.; Luh, T.; Choi, D.; Lin, T. Proc. Natl. Acad. Sci. USA 1997, 94, 9434.

Fatin-Rouge, N.; Toth, E.; Perret, D.; Backer, R. H.; Merbach, A. E.; Bunzli, J.-C. G. J. Am. Chem. Soc. 2000, 122, 10810.

Feng, L.; Zhang, X.; Yu, Z.; Wang, J.; Gu, Z. Chem. Mater. 2002, 14, 4021

Friedman, S. H.; DeCamp, D. L.; Sijbesma, R. P.; Srdanov, G.; Wudl, F.; Kenyon, G. L. J. Am. Chem. Soc. 1993, 115, 6506.

Guldi, D. M.; Hungerbühler, H.; Asmus, K.-D. J. Phys. Chem. 1995, 99, 13487.

Guldi, D. M.; Hungerbühler, H.; Asmus, K.-D. J. Phys. Chem. A 1997, 101, 1783.

Guldi, D. M. J. Phys. Chem. A 1997, 101, 3895.

Hettich, R.; Lahamer, A.; Zhou, L.; Compton, R. Int. J. Mass. Spec. 1999, 182/183, 335.

Hinokuma, K.; Ata, M. Chem. Phys. Lett. 2001, 341, 442.

Hirsch, A. (1994). The Chemistry of the Fullerenes, Georg Thieme Verlag Stuttgart, New York.

Hirsch, A.; Lamparth, I.; Karfunkel, H. R. Angew. Chem. Int. Ed. 1994, 33, 437.

Hoke, S. H. II; Molstad, J.; Yang, S.-S.; Carlson, D.; Kahr, B. J. Org. Chem. 1994, 59, 3230.

Inoue, T.; Kubozono, Y.; Kashino, S.; Takabayashi, Y.; Fujitaka, K.; Hida, M.; Inoue, M.; Kanbara, T.; Emura, S.; Uruga, T. Chem. Phys. Lett. 2000, 316, 381.

Jeng, U.-S.; Lin, T.-L.; Chang, T. S.; Lee, H.-Y.; Hsu, C.-H.; Hsieh, Y.-W.; Canteenwala, T.; Chiang, L. Y. Progr. Colloid Polym. Sci. 2001, 118, 232.

Jeng, U.-S.; Lin, T.-L.; Tsao, C.-S.; Lee, C.-H.; Canteenwala, T.; Wang, L. Y.; Chiang, L. Y.; Han, C. C. J. Phys. Chem. B 1999, 103, 1059.

Kanbara, T.; Kubozono, Y.; Takabayashi, Y.; Fujiki, S.; Iida, S.; Haruyama, Y.; Kashino, S.; Emura, S.; Akasaka, T. Phys. Rev. B 2001, 64, 113403.

Kato, H.; Yashiro, A.; Mizuno, A.; Nishida, Y.; Kobayashi, K.; Shinohara, H. Bioorg. Med. Chem. Lett. 2001, 11, 2935.

Kessler, B.; Bringer, A.; Cramm, S.; Schlebusch, C.; Eberhardt, W.; Suzuki, S.; Achiba, Y.; Esch, F.; Barnaba, M.; Cocco, D. Phys. Rev. Lett. 1997, 79, 2289.

Krätschmer, W.; Lamb, L. D.; Fostiropoulos, K.; Huffman, D. R. Nature 1990, 347, 354.

Kubozono, Y.; Maeda, H.; Takabayashi, Y.; Hiraoka, K.; Nakai, T.; Kashino, S.; Emura, S.; Ukita, S.; Sogabe, T. J. Am. Chem. Soc. 1996, 118, 6998.

Lamparth, I.; Hirsch, A. Chem. Comm. 1994, 1727.

Lamparth, I.; Schick, G.; Hirsch, A. Liebigs Ann./Recueil 1997, 253.

Lauffer, R. B. Chem. Rev. 1987, 87, 901.

Liu, S.; Sun, S. J. Organometallic Chem. 2000, 599, 74.

Mikawa, M.; Kato, H.; Okumura, M.; Narazaki, M.; Kanazawa, Y.; Miwa, N.; Shinohara, H. Bioconj. Chem. 2001, 12, 510.

Mohan, H.; Palit, D. K.; Mittal, J. P.; Chiang, L. Y.; Asmus, K.-D.; Guldi, D. M. J. Chem. Soc., Faraday Trans. 1998, 94, 359.

Nagase, S.; Kobayashi, K.; Akasaka, T. Bull. Chem. Soc. Jpn. 1996, 69, 2131.

Nagase, S.; Kobayashi, K.; Akasaka, T.; Wakahara, T. In Fullerenes Chemistry, Physics, and Technology; Kadish, K. M.; Ruoff, R. S., Eds.; John Wiley & Sons: New York, 2000; 395.

Nierengarten, J.-F.; Nicoud, J.-F. (1997). "Cyclopropanation of C60 with Malonic Acid Mono-Esters," Tet. Lett., 38, 7737-7740.

Ogawa, T.; Sugai, T.; Shinohara, S. J. Am. Chem. Soc. 2000, 122, 3538.

Qingnuan, L.; Yan, X.; Xiaodong, Z.; Ruili, L.; Qieqie, D.; Xiaoguang, S.; Shaoliang, C.; Wenxin, L. Nuclear Med. Biol. 2002, 29, 707.

Sawamura, M., H. Iikura, E. Nakamura, The First Pentahaptofullerene Metal Complexes, J. Am. Chem. Soc. 1996, 118:12850-12851.

Sawamura, M., H. Iikura, T. Ohama, U. Hackler, E. Nakamura, Single-step synthesis of pentaaryl-monohydro[60]fullerenes through fivefold addition of organocopper reagent to C60, J. Orgmetallic Chem. 599 (2000), 32-36.

Shinohara, H.; Yamaguchi, H.; Hayashi, N.; Sato, H.; Ohkohchi, M.; Ando, Y.; Saito, Y. J. Phys. Chem. 1993, 97, 4259.

Shinohara, H. Rep. Prog. Phys. 2000, 63, 843.

Skiebe, A.; Hirsch, A.; Klos, H.; Gotschy, B. Chem. Phys. Lett. 1994, 220, 138.

Solodovnikov, S. P.; Tumanskii, B. L.; Bashilov, V. V.; Lebedkin, S. F.; Skolov, V. I. Russ. Chem. Bull. 2001, 50, 2242.

Stevenson, S.; Rice, G.; Glass, T.; Harich, K.; Cromer, F.; Jordan, M. R.; Craft, J.; Hadju, E.; Bible, R.; Olmstead, M. M.; Maitra, K.; Fisher, A. J.; Balch, A. L.; Dorn, H. C. Nature 1999, 401, 55.

Sun, D.; Huang, H.; Yang, S.; Liu, Z.; Liu, S. Chem. Mater. 1999, 11, 374.

Suzuki, T.; Maruyama, Y.; Kato, T.; Akasaka, T.; Kobayashi, K.; Nagase, S.; Yamamoto, K.; Funasaka, H.; Takahashi, T. J. Am. Chem. Soc. 1995, 117, 9606.

Thrash, T. P.; Cagle, D. W.; Alford, J. M.; Wright, K.; Ehrhardt, G. J.; Mirzadeh, S.; Wilson, L. J. Chem. Phys. Lett. 1999, 308, 329.

Tóth, E.; Helm, L., Merbach, A. In The Chemistry of Contrast Agents in Medical Magnetic Resonance Imaging; Merbach, A.; Tóth, E., Eds.; John Wiley & Sons: Chichester, 2001; 45-120.

Wedeking, P.; Eaton, S.; Covell, D. G.; Nair, S.; Tweedle, M. F.; Eckelman, W. C. Magn. Res. Imag. 1990, 8, 567.

Wharton, T.; Kini, V. U.; Mortis, R. A.; Wilson, L. J. Tet. Lett. 2001, 42, 5159.

Wilson, L. J. Interface 1999, The Electrochemical Society, Winter, 24.

Wilson, L. J.; Cagle, D. W.; Thrash, T. P.; Kennel, S. J.; Mirzadeh, S.; Alford, J. M.; Ehrhardt, G. J. Coord. Chem. Rev. 1999, 190-192, 199.

Wilson, S. R.; Schuster, D. I.; Nuber, B.; Meier, M. S.; Maggini, M.; Prato, M.; Taylor, R. (2000)a "Organic Chemistry of Fullerenes," in Fullerenes: Chemistry, Physics, and Technology, Kadish, K. M. and Ruoff, R. S. eds., John Wiley & Sons, New York, 91-176.

Wilson, S. R. In Fullerenes Chemistry, Physics, and Technology; Kadish, K. M.; Ruoff, R. S., Eds.; John Wiley & Sons: New York, 2000b; 437.

Yamago, S, H. Tokuyama, E. Nakamura, K. Kikuchi, S. Kananishi, K., Sueki, H., Nakahara, S. Enomoto, F. Ambe, In vivo biological behavior of a water-miscible fullerene: 14C labeling, absorption, distribution, excretion and acute toxicity, Chemistry & Biology 2(6)385-389(1995)

Zhang, S.; Sun, D.; Li, X.; Pei, F.; Liu, S. Fullerene Sci. Tech. 1997, 5, 1635.

Zhou, S.; Burger, C.; Chu, B.; Sawamura, M.; Nagahama, N.; Toganoh, M.; Hackler, U. E.; Isobe, H.; Nakamura, E. Science 2001, 291, 1944.

Scheme 1:
Representative Fullerenes of this invention that exhibit good biodistribution and low aggregation

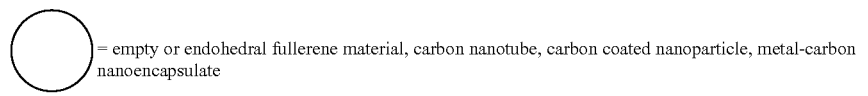

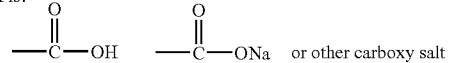

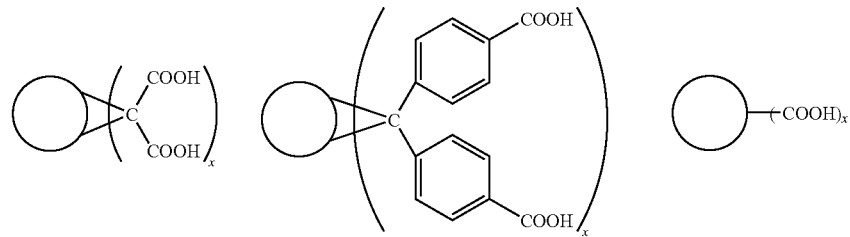

$R_y$ = organic group with a —— COOH functionality attached; y refers to the variable identity/composition of different R groups

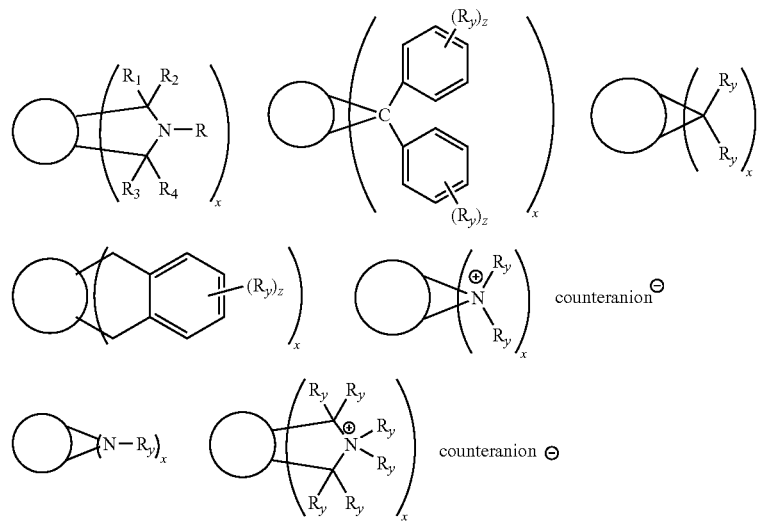

-continued

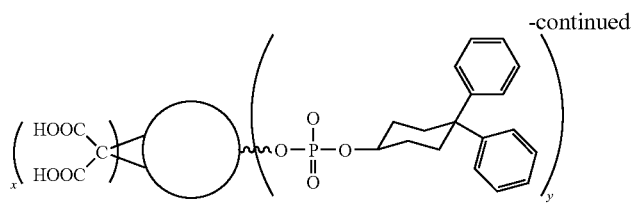

Exemplary carbon nanotube structures with carboxy groups attached

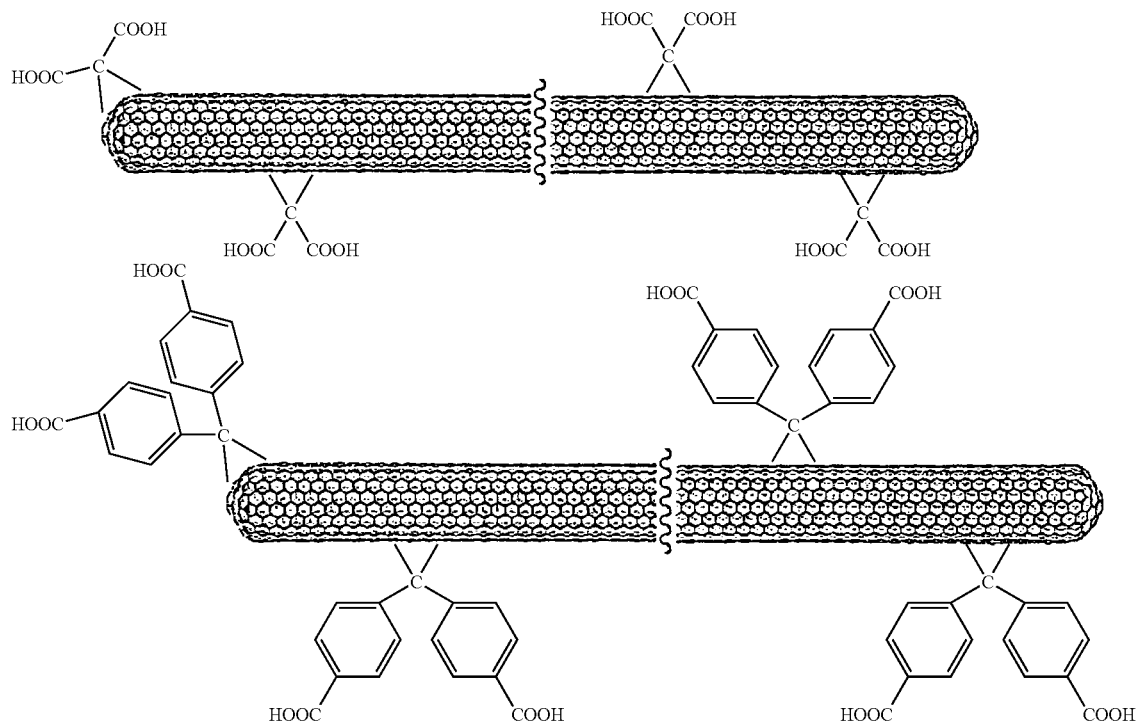

The groups illustrated above on carbon nanotubes can be replaced with any or all of the substituent groups listed on previous pages of Scheme 1. Carbon nanotube includes all single and multi-walled nanotubes, of all different diameters. These nanotubes can also be encapsulating other elements or compounds.

We claim:

1. A method for making a water-soluble fullerene, which exhibits improved biodistribution, which comprises the step of covalently attaching a plurality of functional groups to a fullerene wherein at least ⅙ of the double bonds on the fullerene carry at least one functional group and at least ⅓ of the functional groups on the double bonds are charged groups with the remaining functional groups being non-charged, wherein the fullerene is a metalloendohedral fullerene and where the charged functional groups are >C(COO⁻)n groups where n is 1 or 2.

2. The method of claim 1 wherein the metalloendohedral fullerene is an M@C$_{60}$ class fullerene, where M is any metal.

3. The method of claim 1 wherein the non-charged groups are polar groups.

4. A method for making a water-soluble fullerene, which exhibits improved biodistribution, which comprises the step of covalently attaching a plurality of functional groups to a fullerene wherein at least two of the functional groups are charged functional groups, wherein the fullerene is a metalloendohedral fullerene;

wherein the functional groups are selected from the group consisting of >CR$_1$R$_2$ and >SiR$_1$R$_2$, where R$_1$ and R$_2$ are organic groups independently selected from the group consisting of optionally substituted aryl groups, —COOR$_3$, —O—CO—R$_3$, —CO—NR$_3$R$_4$, —COR$_3$, —CN, —P(O)(OR$_3$)$_2$, SO$_2$R$_3$, and —O—CO—NR$_3$R$_4$, where R$_3$ and R$_4$ are independently selected from hydrogen, an aryl group, an alkyl group, and an alkenyl group, each of which may be substituted with one or more substituents selected from the group consisting of —CO—, —OCO—, and —N(R$_5$)$_2$, where each R$_5$ is selected from the group consisting of hydrogen, an aryl group, an alkyl group, and an alkenyl group; and wherein the water-soluble fullerene has 5 or more >CR$_1$R$_2$ groups covalently bonded to its surface.

5. The method of claim 4 wherein the water-soluble fullerene has 10 or more >CR$_1$R$_2$ groups covalently bonded to its surface.

6. The method of claim 4 wherein the endohedral metal of the metalloendohedral fullerene is one or two magnetic or radioactive metal elements.

7. The method of claim 4, wherein the water-soluble fullerene is a M@C$_{60}$ class fullerene and wherein M is a lanthanide metal having f electrons.

8. The method of claim 7 wherein M is Gd, Y, Eu or Ho.

9. A method for making a water-soluble fullerene, which exhibits improved biodistribution, which comprises the step of covalently attaching a plurality of functional groups to a fullerene wherein at least two of the functional groups are charged functional groups, wherein the fullerene is a metalloendohedral fullerene; and wherein one or more of the functional groups are selected from the group consisting of esters, amides and carbamates.

10. The method of claim 9 wherein the endohedral metal is a radioactive element.

11. The method of claim 9 wherein the endohedral metal is selected from the group consisting of $^{61}$Cu, $^{64}$Cu, $^{67}$Cu, $^{177}$Lu, $^{133}$Xe, $^{141}$Ce, $^{147}$Nd, $^{160}$Tb, $^{161}$Tb, $^{166}$Ho, $^{169}$Er, $^{170}$Tm, $^{175}$Yb, $^{223}$Ra, $^{225}$Ra, $^{225}$Ac, $^{227}$Th, $^{233}$Pa, $^{212}$Bi, $^{213}$Bi, $^{212}$Pb, $^{211}$At, and $^{222}$Rn.

12. The method of claim 9 wherein the metalloendohedral fullerene is a metalloendohedral fullerene having a $C_{60}$, $C_{70}$, $C_{74}$, $C_{82}$ or $C_{84}$ fullerene cage.

13. The method of claim 9 wherein the endohedral metal of the metalloendohedral fullerene is selected from the group consisting of lanthanide metals, actinide metals, transition metals, alkali metals, and alkaline earth metals.

14. The method of claim 13 wherein the endohedral metal is selected from the group consisting of Ce, Pr, Nd, Sm, Eu, Gd, Tb, Dy, Ho, Er, Tm, Tm, Yb, Lu, La, Sc, Y, Ac, Th, Pa, U, Np, Pu, Am, Cu, Zr, Hf, Li, Na, K, Rb, Cs, Be, Mg, Ca, Sr, Ba, and Ra.

15. The method of claim 9 wherein one or more of the plurality of functional groups is selected from the group consisting of a halogen, an OH, an alkyl group, an aryl group, an alkyl-substituted aryl group, an ether group, a polyether group, a polyethylene glycol moiety, a polyethylene oxide moiety, a thioether group, and an alkyl or aryl group substituted with OH, OR, where R is an alkyl or aryl group, or one or more halogens.

16. The method of claim 9 wherein one or more functional groups of the plurality of functional groups is selected from the group consisting of a radiolabel, a fluorescent label and a phosphorescent label.

17. The method of claim 9 wherein at least one functional group is covalently attached to the fullerene employing a cycloaddition reaction.

18. The method of claim 9 wherein at least one functional group is covalently attached to the fullerene employing a cyclopropanation reaction.

19. A method for making a water-soluble fullerene, which exhibits improved biodistribution, which comprises the step of covalently attaching a plurality of functional groups to a fullerene wherein at least two of the functional groups are charged functional groups, wherein the fullerene is a metalloendohedral fullerene, wherein the water-soluble metalloendohedral fullerene has the structure

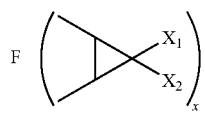

where F is the fullerene and each of $X_1$ and $X_2$ are selected from hydrogen or a functional group, wherein at least two of the functional groups are charged functional groups and x is the number of cyclopropyl groups on the fullerene, and wherein the maximum number of substituents x on the fullerene is equal to the number of double bonds on the fullerene surface prior to addition of the cyclopropyl groups; and wherein x is 5 or more and at least two of the $X_1$ and $X_2$ functional groups are charged groups and wherein the maximum number of substituents x on the fullerene is equal to the number of double bonds on the fullerene surface.

20. The method of claim 19 wherein all of the $X_1$ and $X_2$ functional groups are charged groups.

21. The method of claim 19 wherein x is 4, 5, 6, 7, 8, 9, 10, 11 or 12.

22. A method for making a water-soluble fullerene, which exhibits improved biodistribution, which comprises the step of covalently attaching a plurality of functional groups to a fullerene wherein at least two of the functional groups are charged functional groups, wherein the fullerene is a metalloendohedral fullerene; and wherein the water-soluble fullerene is a metalloendohedral fullerene with 4 to 12 >C(COO$^-$A$^+$)$_2$ or >C(COO$^-$)$_2$B$^{2+}$ groups covalently attached, where A is a monocation and B is a dication.

23. The method of claim 22 wherein the water-soluble fullerene is a metalloendohedral fullerene with 10 to 12 >C(COO$^-$A$^+$)$_2$ or >C(COO$^-$)$_2$B$^{2+}$ groups covalently attached.

24. The method of claim 22 wherein the endohedral metal is Gd.

25. A method for making a water-soluble fullerene, which exhibits improved biodistribution, which comprises the step of covalently attaching a plurality of functional groups to a fullerene wherein at least two of the functional groups are charged functional groups, wherein the fullerene is a metalloendohedral fullerene; and wherein the water-soluble fullerene is a metalloendohedral fullerene with 4 to 12 >C(COO$^-$A$^+$)$_2$ or >C(COO$^-$)$_2$B$^{2+}$ groups and one or more polar or hydrophilic groups covalently attached, where A is a monocation and B is a dication and wherein the maximum number of substituents on the metalloendohedral fullerene is twice the number of double bonds on the surface of the metalloendohedral fullerene prior to covalent attachment of groups.

26. The method of claim 25 wherein the water-soluble metalloendohedral fullerene has the formula M@C$_{2n}$, wherein 10 to 12 >C(COO$^-$A$^+$)$_2$ or >C(COO$^-$)$_2$B$^{2+}$ groups are covalently attached to the metalloendohedral fullerene and wherein the metalloendohedral fullerene is a metalloendohedral fullerene other than one in which 2n is greater than 50, but is less than 60.

27. The method of claim 25 wherein two or more polar or hydrophilic groups are covalently attached to the water-soluble metallofullerene.

28. The method of claim 25 where the polar or hydrophilic groups are OH or a halogen.

29. A method for making a water-soluble fullerene, which exhibits improved biodistribution, which comprises the step of covalently attaching a plurality of functional groups to a fullerene wherein at least two of the functional groups are charged functional groups, wherein at least ⅙ of the double bonds on the fullerene carry at least one functional group and at least ⅓ of the functional groups on the double bonds are charged groups with the remaining functional groups being non-charged, wherein the fullerene is a metalloendohedral fullerene, and wherein one or more functional groups of the plurality of functional groups are selected from the group of non-charged groups consisting of a serinol amide, —C(NHC(CH$_2$OH)$_2$)$_2$, a polyethylene glycol moiety, and a polyethylene oxide moiety.

30. A method for making a water-soluble fullerene, which exhibits improved biodistribution, which comprises the step of covalently attaching a plurality of functional groups to a fullerene wherein at least two of the functional groups are charged functional groups, wherein the fullerene is a metalloendohedral fullerene;

wherein the functional groups are selected from:

OH groups, esters, amides, halogenated alkyl or aryl groups;

alkyl groups, aryl groups, alkyl-substituted aryl groups;

alkyl or aryl groups substituted with one or more carboxylic acid groups, carboxylates, OH or OR' groups, where R' is alkyl or aryl;

—O—CO—R", —CO—N(R") and —O—CO—N(R")$_2$, where R" is an alkyl alkenyl or aryl group which can also be substituted with —CO—, —OCO—, —N(R")$_2$, halogen or OH groups;

ether or ether groups substituted with carboxylic acid groups or carboxylate groups;

thioether, polyether, serinol amide, —C(NHC(CH$_2$OH)$_2$)$_2$, a polyethylene glycol moiety, and a polyethylene oxide moiety;

amino groups (—N(R)$_2$) or quaternary ammonium cations (—N(R)$_4^+$), where R, independent of other R, is hydrogen, alkyl, aryl or alkenyl groups which are optionally substituted with —CO—, —OCO—, —N(R)$_2$, halogen or OH groups; and >CR$_1$R$_2$ or >SiR$_1$R$_2$ where R$_1$ and R$_2$ are organic groups independently selected from the group consisting of optionally substituted aryl groups, —COOR$_3$, —O—CO—R$_3$, —CO—NR$_3$R$_4$, —COR$_3$, —CN, —P(O)(OR$_3$)$_2$, SO$_2$R$_3$, -and O—CO—N R$_3$R$_4$ where R$_3$ and R$_4$ are independently selected from hydrogen, an aryl group, an alkyl group, and an alkenyl group each of which may be substituted with one or more substituents selected from the group consisting of —CO—, —OCO—, and —N(R$_5$)$_2$, where each R$_5$ is selected from the group consisting of hydrogen, an aryl group, an alkyl group, and an alkenyl group, and wherein the water-soluble fullerene further carries at least one halogen group.

31. The method of claim 30 wherein the charged groups are selected from the group consisting of carboxylic acid groups, carboxylates (—COO$^-$), alkyl or aryl groups substituted with one or more carboxylic acid groups or carboxylates, carboxy-substituted phenyl groups, esters or ether groups substituted with carboxylic acid groups or carboxylate groups, amino groups (—N(R)$_2$) or quaternary ammonium cations (—N(R)$_3^+$), alkyl or aryl groups substituted with one or more amino groups (—N(R)$_2$) or quaternary ammonium cations (—N(R)$_3^+$) where each R, independent of any other R in the group, is hydrogen, alkyl, aryl or alkenyl groups.

32. The method of claim 4, wherein the water-soluble fullerene is a M@C$_{60}$ class fullerene and wherein M is a lanthanide metal having f electrons.

33. The method of claim 32 wherein M is Gd, Y, Eu or Ho.

34. The method of claim 9, wherein the water-soluble fullerene is a M@C$_{60}$ class fullerene and wherein M is a lanthanide metal having f electrons.

35. The method of claim 34 wherein M is Gd, Y, Eu or Ho.

36. The method of claim 22, wherein the water-soluble fullerene is a M@C$_{so}$ class fullerene and wherein M is a lanthanide metal having f electrons.

37. The method of claim 36 wherein M is Gd, Y, Eu or Ho.

38. The method of claim 29, wherein the water-soluble fullerene is a M@C$_{60}$ class fullerene and wherein M is a lanthanide metal having f electrons.

39. The method of claim 38 wherein M is Gd, Y, Eu or Ho.

40. The method of claim 1, wherein the water-soluble fullerene is a M@C$_{60}$ class fullerene and wherein M is a lanthanide metal having f electrons.

41. The method of claim 40 wherein M is Gd, Y, Eu or Ho.

* * * * *